(12) United States Patent
Estrov et al.

(10) Patent No.: US 12,357,659 B2
(45) Date of Patent: Jul. 15, 2025

(54) PRODUCTION OF MEGAKARYOCYTES OR PLATELETS FROM MONOCYTES

(71) Applicant: BOARD OF REGENTS, THE UNIVERSITY OF TEXAS SYSTEM, Austin, TX (US)

(72) Inventors: Zeev Estrov, Houston, TX (US); Srdan Verstovsek, Houston, TX (US); Taghi Manshouri, Houston, TX (US); Ivo Veletic, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 17/488,820

(22) Filed: Sep. 29, 2021

(65) Prior Publication Data

US 2022/0096556 A1   Mar. 31, 2022

Related U.S. Application Data

(60) Provisional application No. 63/085,114, filed on Sep. 29, 2020.

(51) Int. Cl.
  *A61K 35/19*  (2015.01)
  *A61P 7/04*  (2006.01)
  *C12N 5/078*  (2010.01)

(52) U.S. Cl.
  CPC ............. *A61K 35/19* (2013.01); *A61P 7/04* (2018.01); *C12N 5/0644* (2013.01)

(58) Field of Classification Search
  CPC .......... A61K 35/19; A61P 7/04; C12N 5/0644
  See application file for complete search history.

(56) References Cited

PUBLICATIONS

Mandl et al., Characterization of the CD14++CD16+ Monocyte Population in Human Bone Marrow, Plos One, 9(11): 1-6. (Year: 2014).*
Pilling et al., Identification of Markers that Distinguish Monocyte-Derived Fibrocytes from Monocytes, Macrophages, and Fibroblasts, Plos One, 4(10): 1-18. (Year: 2018).*
Mason et al., Assessing the value of autologous and allogeneic cells for regenerative medicine, Regen. Med., 4(6): 835-853. (Year: 2009).*
Sleaseman et al. Immunomagnetic Selection of Purified Monocyte and Lymphocyte Populations from Peripheral Blood Mononuclear Cells following Cryopreservation, Clinai and Diagnostic Labratory Immunology, p. 653-658. (Year: 1997).*
O'Grady et al., The long-term preservation of bone marrow, Transfusion, 12(5): 312-316. (Year: 1972).*
Klairmont et al., The Comparative Sensitivity of Immunohistochemical Markers of Megakaryocytic Differentiation in Acute Megakaryoblastic Leukemia, Am J Clin Pathol, 150: 461-467. (Year: 2018).*
Sirad et al., Expression of bcr-abl Abrogates Factor-Dependent Growth of Human Hematopoietic M07E Cells by an Autocrine Mechanism, Blood, 83(6): 1575-1585. (Year: 1994).*
Casati et al., Refinement of the colony-forming unit-megakaryocyte (CFU-MK) assay for its application to pharmaco-toxicological testing, Toxicology in Vitro, 17: 69-75. (Year: 2003).*
Hogge et al., Quantitation and characterization of human megakaryocyte colony-forming cells using a standardized serum-free agarose assay, 96: 790-800. (Year: 1997).*
Noetzli et al., New Insights Into the Differentiation of Megakaryocytes From Hematopoietic Progenitors, Arterioscler Thromb Vasc Biol, 39: 1288-1300. (Year: 2019).*
Nakasone et al. Increased CD83 expression of CD34-positive monocytes in donors during peripheral blood stem cell mobilization in humans. Sci Rep 9, 16499 (2019) (Year: 2019).*
Bucala et al., "Circulating Fibrocytes Define a New Leukocyte Subpopulation That Mediates Tissue Repai", Molecular Medicine, vol. 1, No. 1, Nov. 1994, pp. 71-81.
Debili et al., "Different Expression of Cd41 on Human Lymphoid and Myeloid Progenitors From Adults and Neonates", Blood, vol. 97, No. 7, May 2001, pp. 2023-2030.
Eaves , "Hematopoietic Stem Cells: Concepts, Definitions, and the New Reality", Blood, vol. 125, No. 17, Apr. 23, 2015, pp. 2605-2613.
Groopman , "The Pathogenesis of Myelofibrosis in Myeloproliferative Disorders", Annals of Internal Medicine, vol. 92, No. 6, Jun. 1980, pp. 857-858.
Hamers et al., "Human Monocyte Heterogeneity as Revealed by High-Dimensional Mass Cytometry", Arteriosclerosis Thrombosis and Vascular Biology, vol. 39, No. 1, Jan. 2019, pp. 25-36.
Hopman et al., "Advances in Stem Cell Mobilization", Blood Reviews, vol. 28, No. 1, Jan. 2014, pp. 31-40.
Husheem et al., "Characterization of Circulating Human Osteoclast Progenitors: Development of In Vitro Resorption Assay", Calcified Tissue International, vol. 76, No. 3, Apr. 2005, pp. 222-230.
Kuwana et al., "Human Circulating CD14+ Monocytes as a Source of Progenitors That Exhibit Mesenchymal Cell Differentiation", Journal of Leukocyte Biology, vol. 74, No. 5, Dec. 2003, pp. 833-845.
Law et al., "Analysis of Human Megakaryocytic Cells Using Dual-Color Immunofl Uorescence Labeling", Cytometry, vol. 41, No. 4, Nov. 2000, 17 pages.
Lei et al., "Induction of Differentiation of Human Stem Cells Ex Vivo: Toward Large-scale Platelet Production", World Journal of Stem Cells, vol. 11, No. 9, Sep. 2019, pp. 666-676.

(Continued)

*Primary Examiner* — Taeyoon Kim
*Assistant Examiner* — Nicholas A Humphries
(74) *Attorney, Agent, or Firm* — Kilpatrick Townsend & Stockton LLP

(57) ABSTRACT

We disclose a method, comprising extracting cells from a tissue of a donor, wherein the tissue is selected from the group consisting of blood and bone marrow; isolating $CD14^+$ monocytes from the extracted cells; culturing the isolated $CD14^+$ monocytes; differentiating the cultured $CD14^+$ monocytes into megakaryocytes; and administering, to a patient suffering from a platelet deficiency, at least one cell type selected from the group consisting of the differentiated megakaryocytes and platelets produced by the differentiated megakaryocytes. We also disclose a kit comprising at least one material usable in a method; and instructions to perform a method.

11 Claims, 12 Drawing Sheets

(56) References Cited

PUBLICATIONS

Lundahl et al., "Monocyte and Neutrophil Adhesion to Matrix Proteins Is Selectively Enhanced in the Presence of Inflammatory Mediators", Scandinavian Journal of Immunology, vol. 44, No. 2, Aug. 1996, pp. 143-149.

McLornan et al., "Allogeneic Stem Cell Transplantation for Myelofibrosis in 2012", British Journal of Haematology, vol. 157, No. 4, May 2012, pp. 413-425.

Nakamura et al., "Expandable Megakaryocyte Cell Lines Enable Clinically Applicable Generation of Platelets from Human Induced Pluripotent Stem Cells", Cell Stem Cell, vol. 14, No. 4, Apr. 3, 2014, pp. 535-548.

Nowicka et al., "CyTOF Workflow: Differential Discovery in High-throughput High-Dimensional Cytometry Datasets", vol. 6, No., Nov. 2017, 69 pages.

Passacquale et al., "Monocyte-Platelet Interaction Induces a ProInflammatory Phenotype in Circulating Monocytes", Plos One, vol. 6, No. 10, Available online at: https://www.ncbi.nlm.nih.gov/pmc/articles/PMC3192052/pdf/pone.0025595.pdf, Oct. 2011, 12 pages.

Prieto et al., "Regulated Expression of Integrins and Other Adhesion Molecules During Differentiation of Monocytes Into Macrophages", Cellular Immunology, vol. 156, No., 1, Jun. 1994, pp. 191-211.

Quintas-Cardama et al., "Preclinical Characterization of Atiprimod, A Novel Jak2 and Jak3 Inhibitor", Investigational New Drugs, vol. 29, No. 5, 2011, pp. 816-826.

Rampal et al., "Integrated Genomic Analysis Illustrates the Central Role of JAK-STAT Pathway Activation Inmyeloproliferative Neoplasm Pathogenesis", Blood, vol. 123, No. 22, May 29, 2014, 17 pages.

Reilkoff et al., "Fibrocytes: Emerging Effector Cells in Chronic Inflammation", Nature Reviews Immunology, vol. 11, No. 6, 2011, pp. 427-435.

Stack et al., "Multiplexed Immunohistochemistry, Imaging, and Quantitation: A Review, With an Assessment of Tyramide Signal Amplification, Multispectral Imaging and Multiplex Analysis", Methods, vol. 70, No. 1, Sep. 2014, pp. 46-58.

Stroncek et al., "Platelet Transfusions", Lancet, vol. 370, Aug. 2007, pp. 427-438.

Thiele et al., "European Consensus on Grading Bone Marrow Fibrosis and Assessment of Cellularity", Haematologica, vol. 90, No. 8, Apr. 2005, pp. 1128-1132.

Thiele et al., "Grade of Bone Marrow Fibrosis Is Associated With Relevant Hematological Findings—a Clinicopathological Study on 865 Patients With Chronic Idiopathic Myelofibrosis", Annals of Hematology, vol. 85, No. 4, Apr. 2006, pp. 226-232.

Vannucchi, "A Pathobiologic Pathway linking Thrombopoietin, GATA-1, and TGF-beta 1 in the Development of Myelofibrosis", Blood, vol. 105, No. 9, May 1, 2005, pp. 3493-3501.

Vener et al., "Prognostic Implications of the European Consensus for Grading of Bone Marrow Fibrosis in Chronic Idiopathic Myelofibrosis", Blood, vol. 111, No. 4, Feb. 15, 2008, pp. 1862-1865.

Verstovsek et al., "A Double-Blind Placebo-Controlled Trial of Ruxolitinib for Myelofibrosis", The New England Journal of Medicine, vol. 366, No. 9, Mar. 1, 2012, pp. 799-807.

Verstovsek et al., "Role of Neoplastic Monocyte-derived Fibrocytes in Primary Myelofibrosis", Journal of Experimental Medicine, vol. 213, No. 9, Aug. 2016, pp. 1723-1740.

Williamson et al., "Challenges in the Management of the Blood Supply", The Lancet, vol. 381, May 2013, pp. 1866-1875.

* cited by examiner

PRODUCTION OF MEGAKARYOCYTES OR PLATELETS FROM MONOCYTES

CROSS-REFERENCE TO RELATED APPLICATIONS

This application claims priority to and the benefit of U.S. Provisional Patent Application Ser. No. 63/085,114, filed Sep. 29, 2020, the contents of which are incorporated herein by this reference as if fully set forth herein.

FIELD OF THE INVENTION

The present invention relates generally to the field of treatment of platelet deficiency. More particularly, it concerns the preparation in vitro of megakaryocytes or platelets produced by such megakaryocytes.

BACKGROUND OF THE INVENTION

Platelets are essential for regulation of thrombosis and hemostasis, inflammation, and innate immunity. Platelets function in response to injury by forming clots to stop bleeding. Platelet transfusions are necessary in individuals with thrombocytopenia (low platelet counts). Thrombocytopenia is often encountered in cancer patients treated with high-dose chemotherapy, those suffering from hematological malignancies or bone marrow failure, as well as in cases of severe hemorrhage, trauma and wounds, surgery, and hematopoietic stem cell transplantation.

In recent years, the demand for platelets has been rising due to the increasing rates of cancer and aging population, resulting in a highly unmet need. More than 4.5 million units of platelets are transfused in the US and Europe annually (Stroncek D F and Rebulla P. Platelet transfusions. Lancet. 2007; 370:427-438); however, platelet supply is limited and allogeneic blood donations are the exclusive source of platelets at present. Platelet shortage is further exacerbated by other practical limitations: a. fresh platelets have a short shelf life (3-7 days) (Williamson L M, Devine D V. Challenges in the management of the blood supply. Lancet. 2013; 381: 1866-1875), they must be kept with plasma at 20-24° C., thus, they are susceptible to pathogen contamination, and they readily lose their clotting ability when frozen; b. patients develop platelet refractoriness because chronic transfusions result in production of antibodies against human platelet antigens or human leucocyte antigens on the transfused platelets.

Platelets are produced in vivo by megakaryocytes in bone marrow. The extraction of megakaryocytes from bone marrow is invasive, requiring penetration of donor bone.

Some researchers have attempted to produce platelets by generating megakaryocytes. To date, two main techniques for forming megakaryocytes have been proposed in the literature (Nakamura S., Takayama N., Hirata S., et al. Expandable megakaryocyte cell lines enable clinically applicable generation of platelets from human induced pluripotent stem cells. Cell Stem Cell. 2014; 14:535-548; Kuwana M., Okazaki Y. Kodama H., et al. Human circulating $CD14^+$ monocytes as a source of progenitors that exhibit mesenchymal cell differentiation. J. Leukocyte Biology. 2003; 74:833-845; Lei X., Yang Y-Q., Ma C-Y., et al. Induction of differentiation of human stem cells ex vivo: Toward large-scale platelet production. World J Stem Cells. 2019; 11 (9):666-676):

a. Human Induced Pluripotent Stem Cells (iPS): pluripotent stem cells generated directly from somatic cells (through de-differentiation). This first step is followed by a second step where the pluripotent stem cells are differentiated into hematopoietic stem cells and then to megakaryocytes. The technology of generating human iPS suffers from low efficiency and poses significant risks because the derived cells can become mutagenic and, at least theoretically, carcinogenic (the procedure may activate oncogenes).

b. Human pluripotent stem cells (HSC) are differentiated to immature megakaryocytes, which are expanded and undergo polyploidization in culture, and then generate mature megakaryocytes. This procedure is tedious and is not clinically applicable as the number of bone marrow HSC is extremely low. Furthermore, the megakaryocytes produced in this way were found to harbor a significantly lower capacity to undergo polyploidization in culture as compared to bone marrow-derived platelets.

The processes that have been proposed up to the present are not clinically applicable and have significant hurdles. Human iPS technology suffers from low efficiency and poses significant risks due to the possibility of tumorigenicity of the derived cells. The use of HSC also has low efficiency of platelet production.

Thus, it would be desirable to generate platelets from cells that are easily harvested from a donor's body or tissues, are clinically applicable, have high efficiency of platelet production; wherein the cells and/or the platelets are readily generated and/or preserved; and/or wherein the cells and/or the platelets are oncogene- and pathogen-free.

SUMMARY OF THE INVENTION

The following presents a simplified summary of the invention in order to provide a basic understanding of some aspects of the invention. This summary is not an exhaustive overview of the invention. It is not intended to identify key or critical elements of the invention or to delineate the scope of the invention. Its sole purpose is to present some concepts in a simplified form as a prelude to the more detailed description that is discussed later.

In one embodiment, the present invention relates to a method, comprising extracting cells from a tissue of a donor, wherein the tissue is selected from the group consisting of blood and bone marrow; isolating $CD14^+$ monocytes from the extracted cells; culturing the isolated $CD14^+$ monocytes; differentiating the cultured $CD14^+$ monocytes into megakaryocytes; and administering, to a patient suffering from a platelet deficiency, at least one cell type selected from the group consisting of the differentiated megakaryocytes and platelets produced by the differentiated megakaryocytes.

In one embodiment, the present invention relates to a method, comprising extracting cells from a tissue of a donor, wherein the tissue is selected from the group consisting of blood and bone marrow; isolating $CD14^+$ monocytes from the extracted cells; and performing at least one action selected from the group consisting of cryopreserving the extracted cells prior to the isolating and cryopreserving the $CD14^+$ monocytes after the isolating.

In one embodiment, the present invention relates to a kit, comprising at least one material selected from the group consisting of a first vessel configured to confine blood, a second vessel configured to confine aspirated bone marrow, a third vessel configured to confine a biochemical or biological solution or suspension, a first solution for isolation of cells from blood or bone marrow, a second solution for cryopreserving cells suspended therein, a fourth vessel configured to store a suspension of cells in the second solution at a temperature at or below about −80° C., a third solution for washing cells, a first antibody against a CD14 of a first species, a plurality of magnetic microbeads comprising on outer surfaces thereof a second antibody against a CD14 of the first species, and a cell separation column configured to receive the plurality of magnetic microbeads; and instructions to perform a method comprising: extracting cells from a tissue of a donor, wherein the tissue is selected from the group consisting of blood and bone marrow; isolating CD14$^+$ monocytes from the extracted cells; and performing at least one action selected from the group consisting of cryopreserving the extracted cells prior to the isolating and cryopreserving the CD14$^+$ monocytes after the isolating.

The monocytes, the megakaryocytes differentiated therefrom, and/or the platelets produced therefrom, may be usable in generating platelets from cells that are easily harvested from a donor's body or tissues, are clinically applicable, have high efficiency of platelet production; wherein the cells and/or the platelets are readily generated and/or preserved; and/or wherein the cells and/or the platelets are oncogene- and pathogen-free.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

Figure 1:
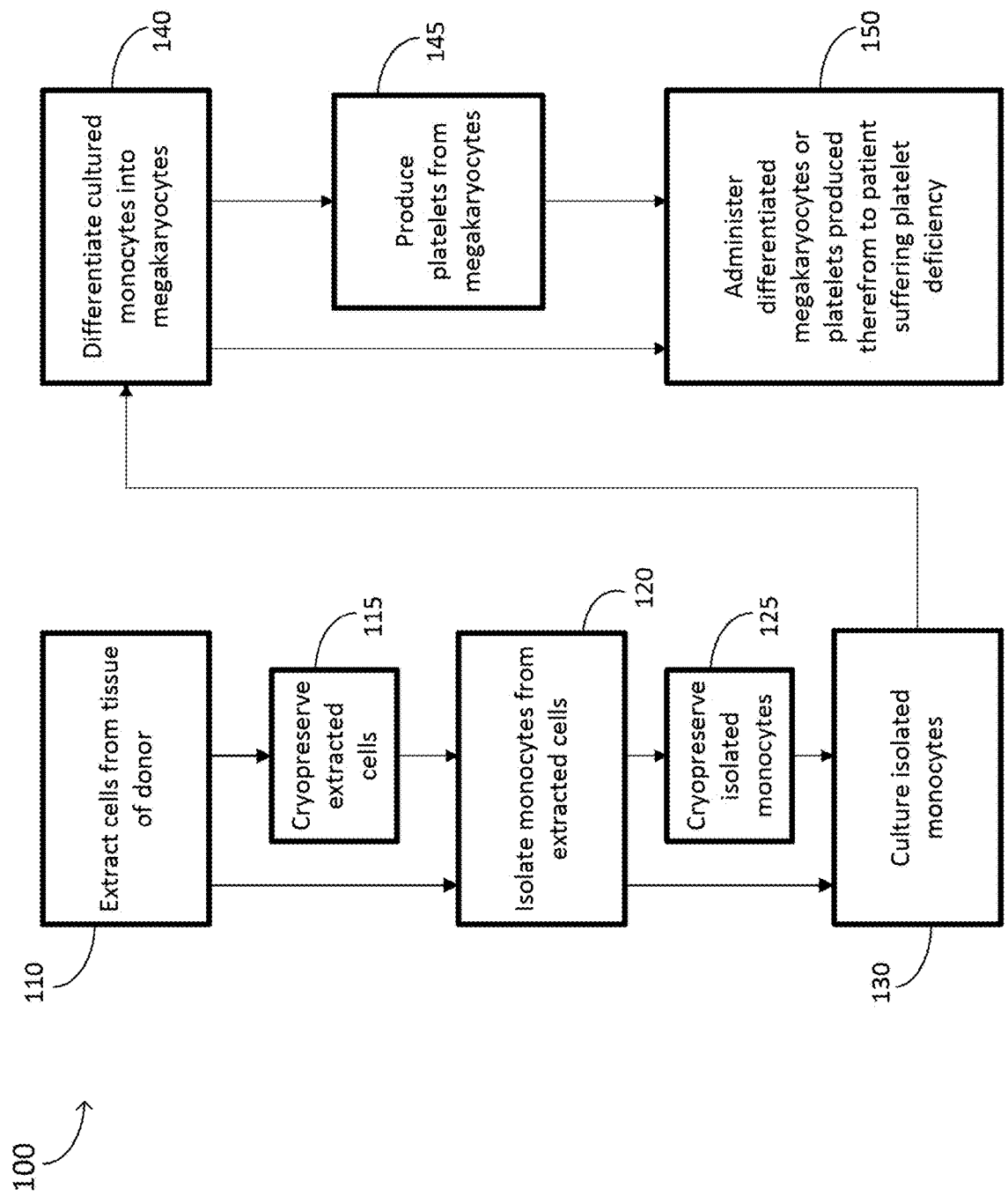
FIG. 1 presents a flowchart of a first method in accordance with embodiments herein.
Figure 2:
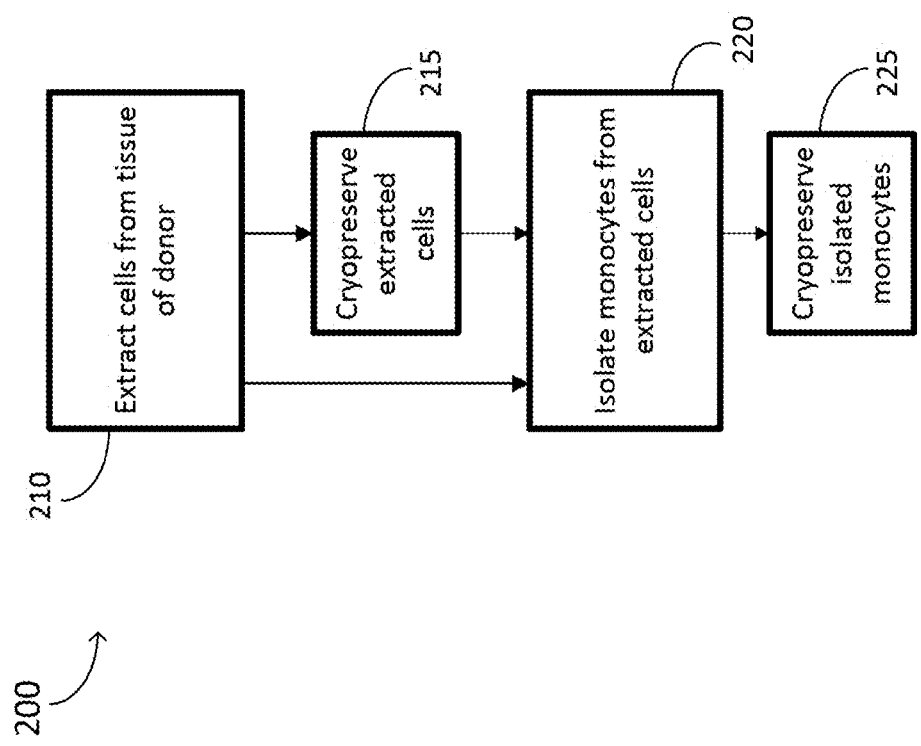
FIG. 2 presents a flowchart of a second method in accordance with embodiments herein.

While the subject matter disclosed herein is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims. Moreover, the stylized depictions illustrated in the drawings are not drawn to any absolute scale.

DESCRIPTION OF ILLUSTRATIVE EMBODIMENTS

Various illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related, regulatory, and business-related constraints, which will vary from one implementation to another. Moreover, it will be appreciated that such a development effort might be complex and time-consuming but would nevertheless be a routine undertaking for those of ordinary skill in the art having the benefit of this disclosure.

The present subject matter will now be described with reference to the attached figures. Various structures, systems, and devices are schematically depicted in the drawings for purposes of explanation only and so as to not obscure the present disclosure with details that are well known to those skilled in the art. Nevertheless, the attached drawings are included to describe and explain illustrative examples of the present disclosure. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, any given numerical value includes the inherent variation of error for the device or the method being employed to determine the value, or the variation that exists between study subjects or healthcare practitioners.

FIG. 1 presents a flowchart of a method 100 in accordance with embodiments of the present disclosure. The method 100 comprises extracting (at 110) cells from a tissue of a donor, wherein the tissue is selected from the group consisting of blood and bone marrow.

The donor may be any mammal. In one embodiment, the donor may be patient suffering or at risk of suffering from a platelet deficiency. Examples of causes of platelet deficiency include, but are not limited to, aplastic anemia, immune thrombocytopenia, and high-dose chemotherapy for cancer.

In other embodiments, the donor may be a first individual and a patient may be a second individual. The donor may be a healthy individual and the patient may be a person suffering from a platelet deficiency, such as a platelet deficiency arising from one or more of the exemplary causes set forth above, among others.

In embodiments, the present method may be performed in a veterinary context. That is, the donor may be any non-human mammal and a patient may be a second individual of the same species. The non-human mammal may be a research animal, a pet, livestock, a working animal, a racing animal (e.g., a horse, a dog, a camel, etc.), an animal at stud (e.g., a bull, a retired racing stallion, etc.), or any other non-human mammal for which it is desired to treat a platelet deficiency it suffers from or is at risk of suffering from.

For convenience, the description will typically refer to human donors and patients. However, the person of ordinary skill in the art having the benefit of the present disclosure will readily be able to adapt the teachings of the present disclosure to a veterinary context.

Specific techniques for extracting cells from blood, such as peripheral blood and bone marrow are known. For example, blood containing cells may be collected from a vein by well-known phlebotomy techniques. Bone marrow containing cells may be collected from bone marrow by introducing a syringe into a bone, such as the iliac crest of the pelvis, and aspirating bone marrow into a collection vessel. Specific implementation details will be known to the person of ordinary skill in the art and need not be described further.

Cells may be extracted from the collected blood or bone marrow by any appropriate technique that preferentially extracts low-density cells, which will be expected to comprise monocytes. In one embodiment, the cells may be extracted by centrifugation of the collected blood or bone marrow, to yield a cell-enriched precipitate; layering the cell-enriched precipitate on a first solution for isolation of cells from blood or bone marrow, such as FICOLL-PAQUE® (GE Healthcare Bio-Sciences AB, Uppsala, Sweden); and centrifugation, to yield a layer comprising low-density cells. Additional cell wash and storage steps may be performed, as will be known to the person of ordinary skill in the art.

In embodiments wherein the cells are extracted (at 110) from blood, the cells may conveniently be extracted (at 110) from the buffy coats of blood donated as part of existing blood banking infrastructure. Buffy coats are usually discarded, but the present disclosure allows for the use thereof.

In one embodiment, the method 100 may comprise cryopreserving (at 115) the extracted cells. For example, cryopreserving (at 115) may comprise suspending low-density cells in a second solution for cryopreserving cells suspended therein and adding the suspension of the low-density cells to a vessel configured to store suspensions of cells in the second solution at a temperature at or below about 80° C. Subsequently, in one embodiment, the cell suspension may be cryopreserved (at 115) at about −80° C. for up to about 48 hr. In another embodiment, the cell suspension may be cryopreserved (at 115) at from about −190° C. to about −210° C. Such temperatures may be achieved by cryopreserving (at 115) in liquid nitrogen.

Regardless of whether cryopreserving (at 115) is performed, the method 100 further comprises isolating (at 120) $CD14^+$ monocytes from the extracted cells. By "$CD14^+$ monocytes" is meant monocytes expressing CD14 on the cell surfaces thereof. In one embodiment, the $CD14^+$ monocytes may further exhibit a $CD34^-$ phenotype, i.e., the monocytes do not express CD34 on the cell surfaces thereof.

Isolation of monocytes may be achieved by the person of ordinary skill in the art having the benefit of the present disclosure using known techniques. In one embodiment, the isolating (at 120) comprises centrifuging low-density cells previously extracted (at 110) (after thawing the extracted cells, if the extracted cells were cryopreserved (at 115) prior to isolating (at 120)), to yield a cell-enriched precipitate; incubating the cells with a first antibody against a CD14 of the donor's species or a plurality of magnetic microbeads comprising on outer surfaces thereof a second antibody against a CD14 of the donor's species; and sorting the cells bound by the first or second antibody from all other cells not bound by the antibody, e.g., by fluorescence-activated cell sorting (FACS) or a magnetic sorting column, to yield isolated $CD14^+$ monocytes. Exemplary antibodies that may be used include, but are not limited to, anti-CD14 (PerCP-CY5.5) and anti-CD34 (FITC) antibodies. Additional cell wash and storage steps may be performed. Other techniques of isolating monocytes, and in particular embodiments, $CD14^+$ monocytes, will be apparent to the person of ordinary skill in the art having the benefit of the present disclosure.

In one embodiment, the method 100 may comprise cryopreserving (at 125) the isolated monocytes. For example, cryopreserving (at 125) may comprise suspending isolated monocytes in the second solution referred to above for cryopreserving cells suspended therein and adding the suspension of the isolated monocytes to a vessel configured to store suspensions of cells in the second solution at a temperature at or below about 80° C. Subsequently, in one embodiment, the isolated monocyte suspension may be cryopreserved (at 115) at about −80° C. for up to about 48 hr. In another embodiment, the isolated monocyte suspension may be cryopreserved (at 115) at from about −190° C. to about −210° C. Such temperatures may be achieved by cryopreserving (at 115) in liquid nitrogen.

Whether or not the isolated monocytes are cryopreserved (at 125), the method 100 also comprises culturing (at 130) the isolated $CD14^+$ monocytes. "Culturing" is used herein to refer to maintaining and growing cells in vitro. Techniques for culturing monocytes may be as described in the examples below.

The method 100 may also comprise differentiating (at 140) the cultured $CD14^+$ monocytes into megakaryocytes. Techniques for differentiating monocytes into megakaryocytes may be as described in the examples below.

As is known, megakaryocytes produce platelets in sequestered regions of the cytoplasm. The platelets are eventually released. A single megakaryocyte may produce many thousands of platelets. In vivo, most megakaryocytes are found in the bone marrow. However, by following the teachings of the present disclosure, megakaryocytes may be differentiated from monocytes, which may easily be extracted from the blood, in contrast to extraction of megakaryocytes from bone marrow.

After differentiated megakaryocytes have been produced (at 140), the method 100 may comprise producing (at 145) platelets from megakaryocytes in vitro. Techniques for producing platelets from megakaryocytes are known to the person of ordinary skill in the art having the benefit of the present disclosure and need not be described further.

Regardless of whether platelets are produced (at 145) from megakaryocytes in vitro, the method 100 further comprises administering (at 150), to a patient suffering from a platelet deficiency, at least one cell type selected from the group consisting of the differentiated megakaryocytes and the platelets produced by the differentiated megakaryocytes. "At least one cell type" means that both differentiated megakaryocytes and platelets produced by differentiated megakaryocytes may be administered. Further, cell separation techniques performed on a culture medium or cell suspension comprising both differentiated megakaryocytes and platelets produced by differentiated megakaryocytes, to yield aliquot(s) enriched in differentiated megakaryocytes or platelets produced by differentiated megakaryocytes, may include some of the unintended cell type while still being within the meaning of "at least one cell type."

As stated above, the donor and the patient may be the same individual, in which case administering (at 150) the differentiated megakaryocytes and/or the platelets produced by differentiated megakaryocytes is an autologous transfusion. Alternatively, the donor and the patient may be distinct individuals of the same species, in which case administering (at 150) the differentiated megakaryocytes and/or the platelets produced by differentiated megakaryocytes is an allogeneic transfusion.

In one embodiment, the differentiated megakaryocytes and/or the platelets produced by the differentiated megakaryocytes may be administered in any appropriate composition known for introducing blood or blood products into the circulation of a patient. The composition may further comprise one or more other pharmaceutically-acceptable compounds known for use in blood product delivery, such as buffers, preservatives, adjuvants, surfactants, diluents (e.g. saline or dextrose) or the like. Such particular other compounds may be routinely selected by the person of ordinary skill in the art having the benefit of the present disclosure.

The composition may be administered (at 150) to the patient by any route. Generally, intravenous injection routes may be used. Such routes are well-understood and have relatively low patient discomfort. Alternatively, and more suitably for differentiated megakaryocytes than for platelets, the composition may be administered (at 150) into a bone marrow space of the patient.

In the method 100, administering (at 150) may be performed in a single dose or a plurality of doses. Generally, given that platelets have a relatively low circulatory lifespan (about 7-10 days) and that production of platelets by megakaryocytes is destructive to the megakaryocytes, a plurality of doses may be desirable until the patient's platelet deficiency is resolved, or other causes of platelet deficiency are removed, e.g., if chemotherapy is discontinued. If a plurality of doses is performed, the number of doses and the time between doses can be selected as a routine matter by the person of ordinary skill in the art having the benefit of the present disclosure.

In one embodiment, the present disclosure relates to a method 200. The method 200 comprises extracting (at 210) cells from a tissue of a donor, wherein the tissue is selected from the group consisting of blood and bone marrow. The extracting (at 210) may generally be performed as described above regarding extracting (at 110) in method 100.

The method 200 also comprises isolating (at 220) $CD14^+$ monocytes from the extracted cells. The isolating (at 220) may generally be performed as described above regarding isolating (at 120) in method 100. In one embodiment, the isolated $CD14^+$ monocytes further exhibit a $CD34^-$ phenotype.

The method 200 further comprises performing at least one action selected from the group consisting of cryopreserving (at 215) the extracted cells prior to the isolating and cryopreserving (at 225) the $CD14^+$ monocytes after the isolating. In embodiments, both cryopreserving (at 215) and cryopreserving (at 225) may be performed. The cryopreservings (at 215 and 225) may generally be performed as described above regarding the cryopreservings (at 115 and 125, respectively) in method 100.

In one embodiment, the present disclosure relates to a kit, comprising at least one material selected from the group consisting of a first vessel configured to confine blood, a second vessel configured to confine aspirated bone marrow, a third vessel configured to confine a biochemical or biological solution or suspension, a first solution for isolation of cells from blood or bone marrow, a second solution for cryopreserving cells suspended therein, a fourth vessel configured to store a suspension of cells in the second solution at a temperature at or below about −80° C., a third solution for washing cells, a first antibody against a CD14 of a first species, a plurality of magnetic microbeads comprising on outer surfaces thereof a second antibody against a CD14 of the first species, and a cell separation column configured to receive the plurality of magnetic microbeads; and instructions to perform a method comprising: extracting cells from a tissue of a donor, wherein the tissue is selected from the group consisting of blood and bone marrow; isolating $CD14^+$ monocytes from the extracted cells; and performing at least one action selected from the group consisting of cryopreserving the extracted cells prior to the isolating and cryopreserving the $CD14^+$ monocytes after the isolating.

Our methods to produce monocyte-derived megakaryocytes/platelets are advantageous because: 1. they are a natural process, 2. they are clinically applicable, 3. it is easy to isolate circulating monocytes (from peripheral blood), cryopreserve and expand them when needed, and transfuse them back to the same thrombocytopenic patient (autologous transfusion), and 4. monocytes are easily cryopreserved.

A "kit," as used herein, refers to a package containing the composition, and instructions of any form that are provided in connection with the composition in a manner such that a clinical professional will clearly recognize that the instructions are to be associated with the composition.

"Instructions" typically involve written text or graphics on or associated with packaging of compositions of the invention. Instructions also can include any oral or electronic instructions provided in any manner. Written text or graphics may include a website URL or a QR code encoding a website URL, where other instructions or supplemental information may be provided in electronic form.

The kit may contain one or more containers, which can contain the composition or a component thereof. The kits also may contain instructions for mixing, diluting, or administering the composition. The kits also can include other containers with one or more solvents, surfactants, preservatives, and/or diluents (e.g., normal saline (0.9% NaCl), or 5% dextrose) as well as containers for mixing, diluting, or administering the composition to the patient in need of such treatment. Further, the kit may contain one or more lists of reagents, materials, apparatus, etc. which may be required to perform the method, are not included in the kit, and which are commercially available.

The kit, in one embodiment, may comprise a carrier being compartmentalized to receive in close confinement one or more containers such as vials, tubes, and the like.

The method is described above.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Primary Myelofibrosis Marrow-Derived CD14$^+$/CD34$^-$ Monocytes Induce Myelofibrosis-Like Phenotype in Immunodeficient Mice and Give Rise to Megakaryocytes Abstract To confirm that neoplastic monocyte-derived collagen- and fibronectin-producing fibrocytes induce bone marrow (BM) fibrosis in primary myelofibrosis (PMF), we injected PMF BM-derived fibrocyte-precursor CD14$^+$/CD34$^-$ monocytes into the tail vein of NOD-SCID-$\gamma$ (NSG) mice. PMF BM-derived CD14$^+$/CD34$^-$ monocytes engrafted and induced a PMF-like phenotype with splenomegaly, myeloid hyperplasia with clusters of atypical megakaryocytes, persistence of the JAK2V617F mutation, and BM and spleen fibrosis. As control we used normal human BM-derived CD14$^+$/CD34$^-$ monocytes. These monocytes also engrafted and gave rise to normal megakaryocytes that, like PMF CD14$^+$/CD34$^-$-derived megakaryocytes, expressed HLA-ABC and human CD42b antigens. Using two clonogenic assays, we confirmed that PMF and normal BM-derived CD14$^+$/CD34$^-$ monocytes give rise to megakaryocyte colony-forming cells, suggesting that a subpopulation of BM monocytes harbors megakaryocyte progenitor capacity. Taken together, our data suggest that PMF monocytes induce myelofibrosis-like phenotype in immunodeficient mice and that PMF and normal BM-derived CD14$^+$/CD34$^-$ monocytes give rise to megakaryocyte progenitor cells.

Introduction

Primary myelofibrosis (PMF) is a myeloproliferative neoplasm characterized by progressive bone marrow (BM) fibrosis.[1, 2] In approximately 90% of patients with PMF the Janus kinase pathway is constitutively activated by a mutation either in the Janus kinase-2 (JAK2), calreticulin (CALR), or the thrombopoietin receptor MPL gene.[3] Although the majority of patients treated with the JAK1/2 inhibitor ruxolitinib experience a significant improvement in their quality of life, in most patients ruxolitinib does not inhibit or reverse BM fibrosis, nor does it eradicate the neoplastic clone.[4] Currently, allogeneic hematopoietic cell transplantation remains the only curative therapy however no more than 10% of PMF patients are eligible for this procedure, and in most centers treatment-related mortality is relatively high. [5]

Challenging the dogma that BM fibrosis is induced by mesenchymal stromal cells (MSC) overstimulated by cytokines produced by megakaryocytes and platelets,[6, 7] we found that BM fibrosis in PMF is primarily induced by an expanded population of neoplastic fibrocytes.[8] Fibrocytes are monocyte-derived spindle-shaped fibroblast-like cells that express hematopoietic and MSC surface proteins and, like MSC, fibrocytes produce collagen-I, collagen-III and fibronectin. [8] Although constituting less than one percent of the BM cellularity, fibrocytes are recruited to site of tissue injury where they participate both in tissue repair and remodeling.[9, 10] Like in the BM of patients with PMF, fibrocytes participate in the induction of fibrosis in several tissues including the lung, liver, kidney, heart, eye, and skin.[10]

Because we found that PMF BM low-density cells engrafted in NOD-SCID-$\gamma$ (NSG) mice and induced a PMF-like phenotype,[8] we wondered whether monocytes, the fibrocyte precursors, might elicit a similar effect. We hereby report that purified PMF BM CD14$^+$/CD34$^-$ monocytes engrafted in NSG mice and induced BM fibrosis. Similarly, normal BM CD14$^-$/CD34$^-$ cells engrafted in NSG mice and, like PMF BM CD14$^+$/CD34$^-$ cells, gave rise to human megakaryocytes both in vivo and in vitro.

Materials and Methods

Specimen Processing

Diagnostic BM specimens were obtained from treatment-naïve PMF patients after an MD Anderson Cancer Center Institutional Review Board (MDACC IRB1) approved written informed consent had been obtained. The patients' clinical data are provided in S1 Table.

S1 TABLE

| Patients' characteristics. | | | |
|---|---|---|---|
| Patient | 1 | 2 | 3 |
| Age (years) | 73 | 61 | 63 |
| Sex | Female | Female | Male |
| Diagnosis (WHO 2016 criteria) | PMF | PMF | PMF |
| Time from diagnosis (months) | 0.5 | 2.8 | 1.0 |
| Chronic phase disease | Yes | Yes | Yes |
| BM fibrosis grade (EC 2005 criteria) | MF-2 | MF-2 | MF-2 |
| IPSS risk category | Int-2 | Int-2 | Low |
| Leukocyte count (×109/L) | 20.1 | 13.2 | 13.1 |
| Hemoglobin (g/dL) | 13.1 | 9.8 | 12.9 |
| Platelet count (×109/L) | 44 | 289 | 188 |
| Monocytes (% leukocytes) | 4.0 | 4.3 | 1.0 |
| Circulating blasts (% leukocytes) | 1.0 | 0 | 0 |
| LDH (U/L) | 1147 | 1062 | 1444 |
| Constitutional symptoms | No | Yes | No |
| Hepatosplenomegaly | No | No | No |
| JAK2 (V617F) allele burden (%) | 67.2% | 70.0% | 85.9% |
| Karyotype abnormalities | None | None | None |
| Previous or current treatment | No | No | No |

WHO, World Health Organization;
PMF, primary myelofibrosis;
BM, bone marrow;
EC, European consensus;
IPSS, International Prognostic Scoring System;
LDH, lactate dehydrogenase As controls, normal BM aspirates were obtained from AllCells (Alameda, CA). Low-density cells were fractionated by Ficoll-Paque (GE Healthcare Bioscience AB, Uppsala, Sweden) gradient separation as has been described previously,[8] followed by fluorescence-activated cell sorting (FACS) of CD14$^+$/CD34$^-$ cells using anti-CD14 (PerCP-CY5.5) and anti-CD34 (FITC) antibodies.

Immunophenotype Analysis of the CD14$^+$/CD34$^-$ Cell Population.

The purity of the fractionated CD14$^+$/CD34$^-$ cell population was assessed by flow cytometry (FCM) using anti-CD14 (PerCP) and anti-CD34 (FITC) antibodies. In addi tion, PMF patients' and healthy donors' BM aspirates were further analyzed using antibodies or following 9 cell surface antigens: CD14 (PerCP-Cy5.5), CD34 (FITC), CD45 (Pacific Orange), CD68 (PE), CD3 (APC), HLA-DR (APC-H7), CD41 (PE/Cy7), CD42b (Alexa Fluor 700), and CD61 (BV421) using the FlowJo software v10.5.3 (TreeStar, Ashland, OR) and R-based pipeline for high-dimensional cytometry datasets, as previously described.[11, 12] Briefly, CD14+ cells were gated and the expression of each of the above mentioned surface markers was assessed. The antibodies corresponding isotypes were used as controls. In addition, cell surface marker intensities of 4,000 randomly selected cells were obtained in each sample and mapped to a comparable range using arcsin h transformation with a cofactor of 150. Clusters were computationally defined using the unsupervised self-organizing map (SOM) clustering in the FlowSOM package within the R environment (R Foundation for Statistical Computing, Vienna, Austria). The antibodies and their isotype controls used in our study are listed in S2 Table.

S2 TABLE

Flow cytometry antibodies and isotype controls.

| Name (clone) | Fluorophore | Supplier | Catalog no. |
|---|---|---|---|
| Antibodies | | | |
| CD3 (SK7) | APC | BD Biosciences, San Jose, CA | 340440 |
| CD14 (MφP9) | PerCP | BD Biosciences, San Jose, CA | 340585 |
| CD14 (MφP9) | PerCP-Cy5.5 | BD Biosciences, San Jose, CA | 562692 |
| CD34 (8G12) | FITC | BD Biosciences, San Jose, CA | 348053 |
| CD41 (HIP8) | PE/Cy7 | BioLegend, San Diego, CA | 303718 |
| CD42b (HIP1) | Alexa Fluor 700 | BioLegend, San Diego, CA | 303927 |
| CD45 (HI30) | Pacific Orange | Invitrogen, Waltham, MA | MHCD4530 |
| CD45 (2D1) | PerCP-Cy5.5 | BD Biosciences, San Jose, CA | 340952 |
| CD61 (VIPL2) | BV421 | BD Biosciences, San Jose, CA | 744381 |
| CD68 (Y1/82A) | FITC | BD Biosciences, San Jose, CA | 562117 |
| CD68 (Y1/82A) | PE | BioLegend, San Diego, CA | 333808 |
| HLA-ABC (G46-2.6) | FITC | BD Biosciences, San Jose, CA | 555552 |
| HLA-ABC (G46-2.6) | PE | BD Biosciences, San Jose, CA | 555553 |
| HLA-DR (L243) | APC-H7 | BD Biosciences, San Jose, CA | 641393 |
| Isotype controls | | | |
| IgG1, κ (MOPC-21) | Alexa Fluor 700 | BD Biosciences, San Jose, CA | 557882 |
| IgG1, κ (MOPC-21) | APC | BD Biosciences, San Jose, CA | 555751 |
| IgG1, κ (MOPC-21) | FITC | BD Biosciences, San Jose, CA | 555748 |
| IgG1, κ (MOPC-21) | PE | BD Biosciences, San Jose, CA | 559320 |
| IgG1, κ (MOPC-21) | PE/Cy7 | BioLegend, San Diego, CA | 400125 |
| IgG1, κ (X40) | BV421 | BD Biosciences, San Jose, CA | 562438 |
| IgG1, κ (X40) | PerCP-Cy5.5 | BD Biosciences, San Jose, CA | 347212 |
| IgG1, κ | Invitrogen, Pacific Orange | Waltham, MA | MG130 |
| IgG2a, κ (G155-178) | APC-H7 | BD Biosciences, San Jose, CA | 560897 |
| IgG2b, κ (27-35) | FITC | BD Biosciences, San Jose, CA | 555742 |
| IgG2b, κ (27-35) | PerCP-Cy5.5 | BD Biosciences, San Jose, CA | 558304 |
| IgG2b, κ (MG2b-57) | PE | BioLegend, San Diego, CA | 401208 |
| IgG2b, κ (MPC-11) | PerCP | BioLegend, San Diego, CA | 400336 |

CD, cluster of differentiation;
HLA, human leukocyte antigen;
IgG, immunoglobulin G Engraftment and Evaluation of Human BM-Derived CD14+/CD34− Cells in NSG Mice.

A total of 30 NOD scid gamma mice (NOD.Cg-PrkdcscidIl2rgtm1Wjl/SzJ; Jackson Laboratories, Bar Arbor, ME) were included in this study. All animal studies were carried out in strict accordance to an animal protocol approved by the MD Anderson Cancer Center Instructional Animal Care and Utilization Committee (Protocol Number: 00000787-RN02). The animals were euthanized using carbon dioxide as per our protocol and all efforts were made to minimize suffering. Two million PMF or hematologically normal BM-derived CD14+/CD34− cells were injected into the tail vein of 4-6 weeks old female NOD scid gamma mice. Engraftment was assessed after two weeks and then once a month thereafter by FCM of mouse peripheral blood (PB)

cells using mouse anti-human leukocyte antigen (HLA)-ABC antibody and by allele-specific suppressive quantitative polymerase chain reaction (qASSPCR) analyses for the quantification of the JAK2V617F exon 14 mutation.[13] Following euthanasia, femur BM cells were flushed out and analyzed by FCM using human-specific anti-HLA-ABC (PE), anti-CD45 (PerCP-Cy5.5) and anti-CD68 (FITC) antibodies.

In Situ Analysis of Human BM-Derived $CD14^+/CD34-$ Cells in NSG Mice

Femur, sternum and spleen biopsy samples were taken after the animals were euthanized (median time following transplantation, 12 weeks). BM and spleen biopsy morphological analyses were performed using hematoxylin and eosin (H&E) and silver staining as previously described.[8] The degree of BM fibrosis was blindly assessed according to the European consensus criteria.[14] Engraftment of human cells was further assessed by chromogenic immunohistochemistry (IHC) using human-specific anti-HLA-ABC, anti-CD42b, anti-CD3, anti-CD19 and anti-CD34 antibodies in avidin-biotin-peroxidase detection system with 3,30-diaminobenzidine (DAB) substrate and using nuclear fast red counterstain. Then, HLA-ABC-positive cells were further assessed for megakaryocyte markers (CD41, CD42b) and CD14, or fibrocyte markers (CD45, CD68, procollagen-I) by performing multiplexed fluorescence IHC by tyramide signal amplification (TSA) approach. Specifically, mouse BM sections were stained using two different panels (S3 Table) and imaged at 40× resolution using Polaris multispectral system (PerkinElmer, Waltham, MA).

S3 TABLE

Multiplexed fluorescence immunohistochemistry assays.

| Staining | Megakaryocyte Markers | | Fibrocyte Markers | |
|---|---|---|---|---|
| Order | Target | Fluorophore | Target | Fluorophore |
| 1 | CD41 | Opal 520 | CD68 | Opal 520 |
| 2 | CD42b | Opal 570 | Procollagen type I | Opal 570 |
| 3 | CD14 (SP192) | Opal 690 | CD45 | Opal 690 |
| 4 | HLA-ABC | Opal Polaris 780 | HLA-ABC | Opal Polaris 780 |
| 5 | Nuclei | DAPI | Nuclei | DAPI |

CD, cluster of differentiation;
HLA, human leukocyte antigen;
DAPI, 4',6-diamidino-2-phenylindole To ensure optimal signal separation, each fluorophore and tissue autofluorescence were imaged on separate filters and spectrally unmixed as previously described.[15]

Megakaryocyte Colony Culture Assays

The megakaryocyte colony-forming capacity of PMF (n=12) and normal BM-derived $CD14^+/CD34-$ cells (n=6) was assessed by using two different megakaryocyte colony culture assays. The collagen-based MegaCult-C assay (StemCell Technologies, Vancouver, BC, Canada) was used in accordance with the manufacturer's instructions with slight modifications. In brief, 40,000 $CD14^+/CD34-$ cells were cultured in collagen-containing medium in triplicate in the presence of recombinant human thrombopoietin (TPO; 50 ng/mL), interleukin-3 (IL-3; 10 ng/mL) and IL-6 (10 ng/mL). Colony-forming unit-megakaryocyte (CFU-Meg) colonies were fixed after 12 days of culture, stained with anti-CD42b (Vector Blue) antibodies, counterstained with nuclear fast red, and counted using BX43 upright brightfield microscope (Olympus, Tokyo, Japan). A CFU-Meg colony was defined as a cluster of 3 or more nucleated CD42b+ cells. In addition, to further assess antigen co-localization, cells were stained with fluorescent actin (Alexa Fluor 488 phalloidin), CD42b (Alexa Fluor 594) and CD14 (Alexa Fluor 647) antibodies with 40,6-diamidino-2-phenylindole (DAPI) as the nuclear counterstain.

A previously described, slightly modified methylcellulose CFU-Meg colony culture assay was also used.[8] Briefly, $2 \times 10^5$ PMF or normal BM-derived $CD14^+$ cells were mixed with 0.8% methylcellulose in Iscove's modified Dulbecco's medium (Invitrogen, Grand Island, NY) supplemented with 10% fetal calf serum (Invitrogen) and 10 ng/mL thrombopoietin. 500 mL of the mix was incubated in Petri dishes at 37° C. in a humidified atmosphere of 5% CO2 in air. CFU-Meg colonies were scored at day 21 of culture using the Diaphot ELWD 0.3 inverted phase-contrast microscope (Nikon, Tokyo, Japan). A CFU-Meg colony was defined as a cluster of more than 10 large translucent cells or adjacent clusters or 3 or more translucent cells. Single colonies were microaspirated, cytospun onto glass slides and analyzed after May-Grünwald-Giemsa (MGG) staining and immunolabeling with anti-CD42b (DAB) antibodies as described above. To assess differences between colony numbers, the Prism v7.03 software (GraphPad, San Diego CA) was used. Groups were compared using Student's t-test and P<0.05 was considered statistically significant. Fluorescence images were acquired using the Andor Revolution XDi WD spinning disk confocal system with Zyla 4.2 sCMOS camera (Andor Technology, Belfast, UK) and UPlanSApo 30XS silicone oil-immersion objective lens (Olympus, Tokyo, Japan), and adjusted for visual presentation using Imaris v9.1.0 software (Bitplane, Zurich, Switzerland). Antibodies and detection reagents used in the cellular imaging are listed in S4 Table.

S4 TABLE

Cellular imaging detection reagents and antibodies

| Name (clone or conjugate) | Supplier | Catalog no. |
|---|---|---|
| Primary antibodies | | |
| CD3 (MRQ-39) | Cell Marque, Rocklin, CA | 103R-94 |
| CD14 (SP192) | Abcam, Cambridge, United Kingdom | ab183322 |
| CD14 (1H5D8) | Abcam, Cambridge, United Kingdom | ab181470 |
| CD19 (MRQ-36) | Cell Marque, Rocklin, CA | 119M-14 |
| CD34 | Novus Biologicals, Centennial, CO | NBP2-38321 |
| CD41 (M148) | Abcam, Cambridge, United Kingdom | ab11024 |
| CD42b (EPR6995) | Abcam, Cambridge, United Kingdom | ab134087 |
| CD45 (MEM-28) | Abcam, Cambridge, United Kingdom | ab8216 |
| CD68 (KP1) | Abcam, Cambridge, United Kingdom | ab955 |
| HLA-ABC (EMR8-5) | Abcam, Cambridge, United Kingdom | ab70328 |
| Procollagen-I (M-58) | Abcam, Cambridge, United Kingdom | ab64409 |

S4 TABLE-continued

Cellular imaging detection reagents and antibodies

| Name (clone or conjugate) | Supplier | Catalog no. |
|---|---|---|
| Secondary antibodies | | |
| Broad spectrum IgG (HRP) | Invitrogen, Waltham, MA | 87-8963 |
| Mouse/rabbit IgG (HRP) | Vector Laboratories, Burlingame, CA | PK-6200 |
| Rabbit IgG (AP) | Vector Laboratories, Burlingame, CA | AK-5001 |
| Rabbit IgG (Alexa Fluor 594) | Invitrogen, Waltham, MA | A21207 |
| Mouse IgG (Alexa Fluor 647) | Invitrogen, Waltham, MA | A31571 |
| Fluorescent detection reagents | | |
| Phalloidin (Alexa Fluor 488) | Invitrogen, Waltham, MA | A12379 |
| DAPI | Invitrogen, Waltham, MA | D3571 |
| Opal 520 | PerkinElmer, Waltham, MA | FP1487001KT |
| Opal 570 | PerkinElmer, Waltham, MA | FP1488001KT |
| Opal 690 | PerkinElmer, Waltham, MA | FP1497001KT |
| Opal Polaris 780 | PerkinElmer, Waltham, MA | FP1501001KT |
| Chromogenic detection reagents | | |
| DAB | Vector Laboratories, Burlingame, CA | SK-4100 |
| Vector Blue | Vector Laboratories, Burlingame, CA | SK-5300 |
| Shandon Wright-Giemsa | Thermo Scientific, Waltham, MA | 99-907-10 |
| Nuclear fast red | Ricca Chemical, Arlington, TX | R5463200-500A |

Figure 3:
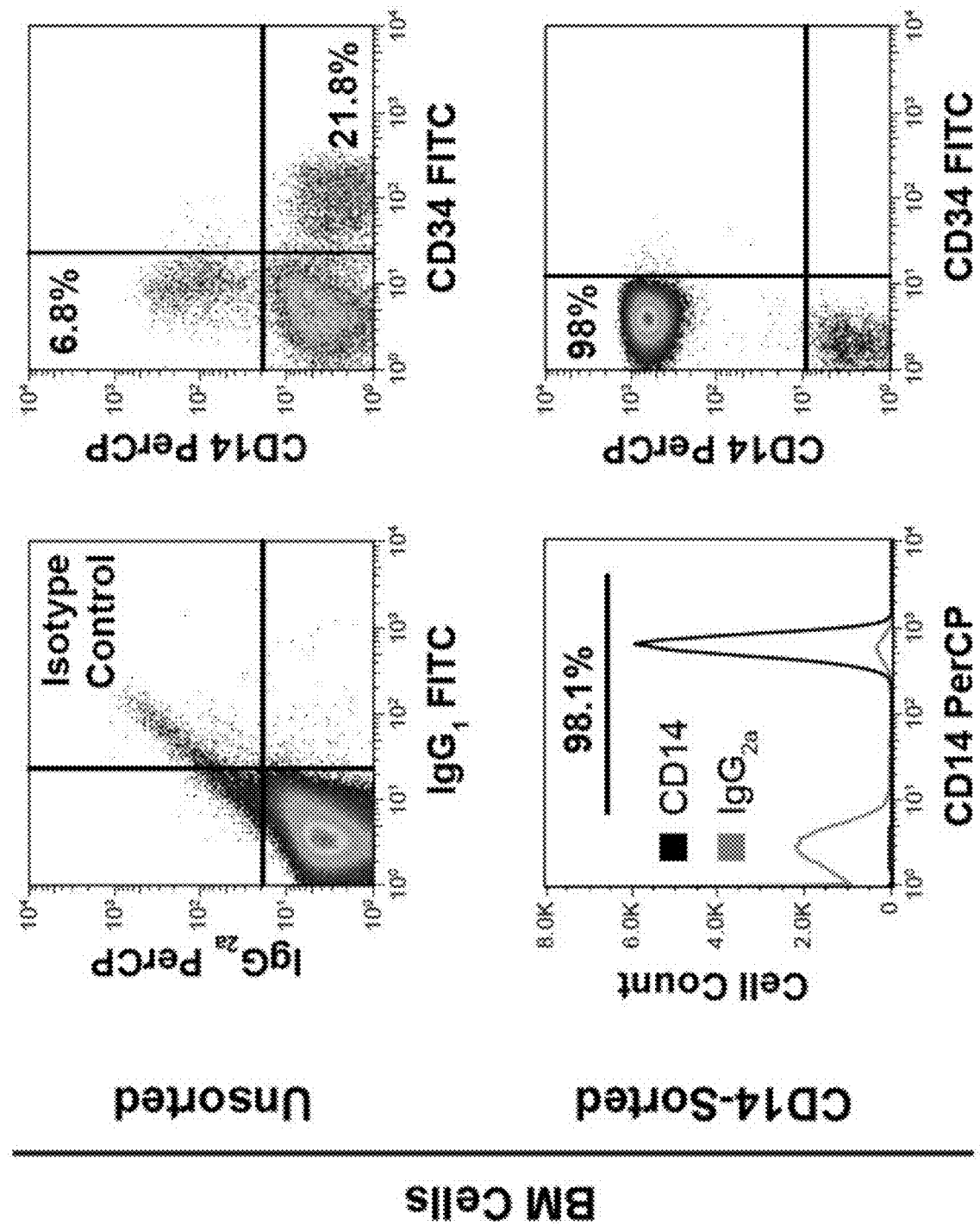
FIG. 3 presents data relating to fractionation and characterization of CD14$^+$/CD34$^-$ monocytes in Example 1. Flow cytometry (FCM) analysis of unsorted PMF and normal donor BM-derived low-density cells using anti-immunoglobulin G2a (IgG2a) and anti-IgG1 isotype control antibodies (left upper panel), and anti-CD14/anti-CD34 monoclonal antibodies (right upper panel) shows that PMF BM CD14$^+$ cells do not express the CD34 antigen. In addition, FCM analysis of FACS-sorted PMF BM-derived cells showed that 98.1% of the sorted cells were CD14-positive (left lower panel) and that the sorted CD14$^+$ cells were CD34$^-$ (right lower panel). Representative single-sample data from experiments performed using 3 different PMF and 2 normal BM cells are depicted.

CD, cluster of differentiation;
HLA, human leukocyte antigen;
IgG, immunoglobulin G;
HRP, horseradish peroxidase;
AP, alkaline phosphatase;
DAPI, 4',6-diamidino-2-phenylindole;
DAB, 3,3'-diaminobenzidine Results and Discussion We have recently found that PMF BM-derived neoplastic fibrocytes induced BM fibrosis. Furthermore, we demonstrated that PMF BM low-density cells engrafted in NSG mice and induced BM and spleen fibrosis.[8] Because fibrocytes are monocyte derived, we wondered whether PMF BM monocytes, would induce BM fibrosis in NSG mice. Using FCM we analyzed PMF and normal donor BM low-density cells and found that $CD14^+$ cells do not express the CD34 antigen (FIG. 3). Then, using FACS sorting we isolated $CD14^+$ BM monocytes from PMF patients' BM aspirates (n=3) and, as control, from BM aspirates of healthy individuals (n=2). Of the $CD14^+$ BM cells, 97.6±1.0% were $CD14^+/CD34-$ (FIG. 3), indicating that the FACS-sorted $CD14^+$ cell population was devoid of CD34+ progenitor cells [16] (FIG. 3; right lower panel).

Figure 4:
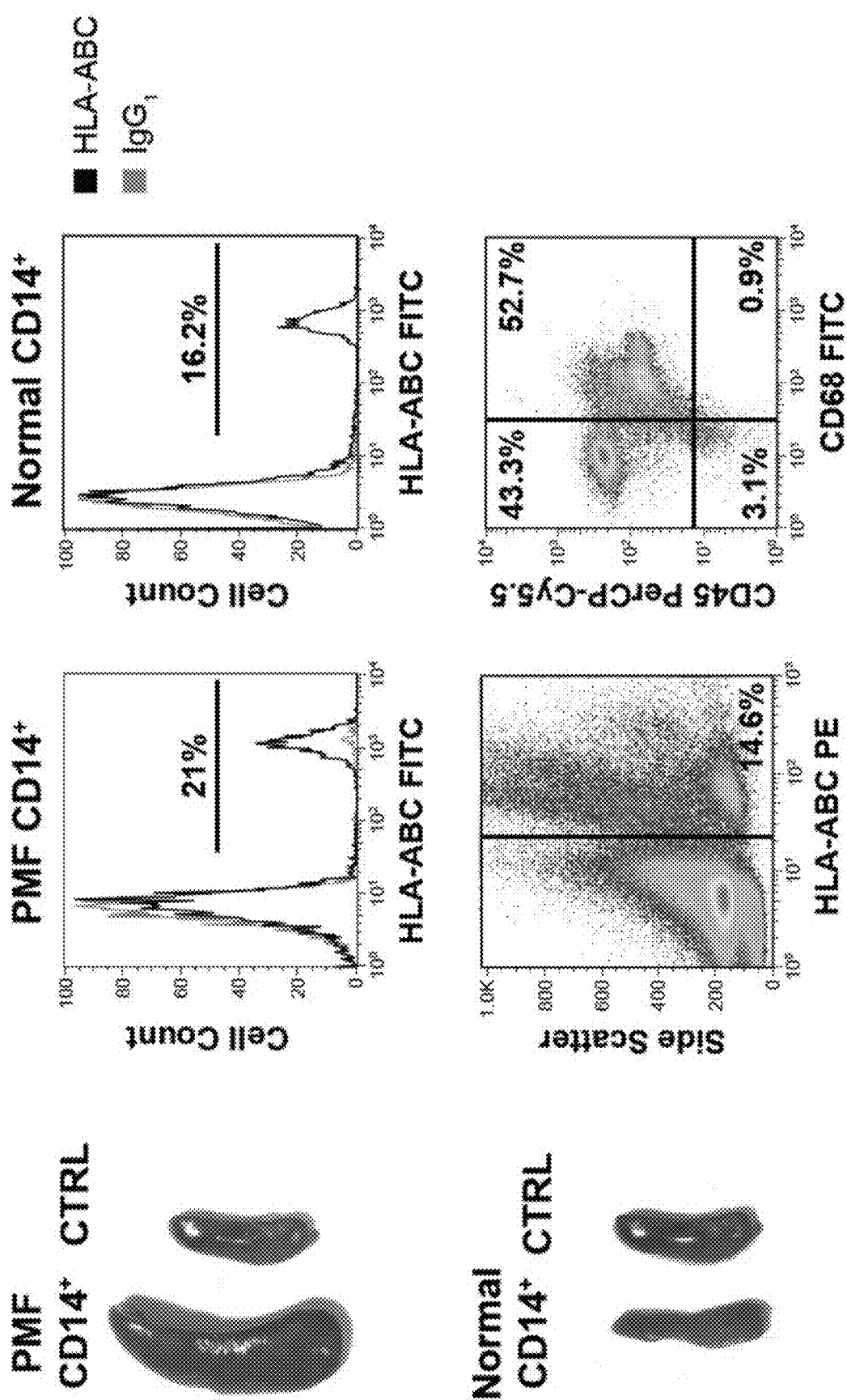
FIG. 4 indicates CD14$^+$/CD34$^-$ monocytes engraft in NSG mice and PMF, but not normal, BM-derived monocytes induce a PMF-like phenotype, as discussed in Example 1. Two months after transplantation, 3 mice injected with PMF BM-derived monocytes and 1 mouse injected with normal BM-derived monocytes were euthanized. Shown is a typical large spleen found in all mice transplanted with PMF BM-derived CD14$^+$/CD34$^-$ monocytes at 1, 2, 3, 4, and 5 months after transplantation but not in mice transplanted with normal BM-derived CD14$^+$/CD34$^-$ cells or untransplanted mice (left panel). CTRL, control untransplanted mice. HLA-ABC+ cells detected in the PB of all transplanted mice (middle and right upper panel), and in the BM of mice transplanted with PMF CD14$^+$/CD34$^-$ cells (left lower panel), 50% of which co-expressed human CD45 and human CD68 (right lower panel) are shown.

To determine whether PMF patients' $CD14^+$ cells induce BM fibrosis in NSG mice, we isolated $CD14^+/CD34-$ BM-derived monocytes from 3 PMF patients and 5 healthy donors and injected the PMF-derived monocytes into 15 NSG mice and normal $CD14^+/CD34-$ monocytes into 5 NSG mice using the protocol of our previously described xenograft mouse model.[8] Ten uninjected mice were used as control. After two weeks and every 4 weeks thereafter, the mice were bled, and their PB cells were assessed for the presence of HLA-ABC antigen by using flow cytometry. HLA-ABC+ cells were detected in the PB of all transplanted mice, but not in control untransplanted mice, until they were euthanized. Two months after transplantation, three mice transplanted with PMF $CD14^+/CD34-$ cells and one mouse transplanted with normal BM $CD14^+/CD34-$ cells were euthanized. Whereas PB HLA-ABC+ cells were detected in all animals of both groups (FIG. 4, middle and right upper panels), enlarged spleens were found in PMF but not in normal $CD14^+/CD34-$ transplanted mice at 1, 2, 3, 4, or 5 month after transplantation (FIG. 4; left panel). Remarkably, 14.3% of BM cells obtained from mice transplanted with PMF $CD14^+/CD34-$ monocytes expressed HLA-ABC and 50% of the HLA-ABC+ cells coexpressed human CD45 and human CD68 antigens (FIG. 4; middle and right lower panels). Taken together, these data suggest that similar to PMF and normal BM low-density cells,[8] BM-derived $CD14^+/CD34-$ cells engraft in NSG mice.

Figure 5:
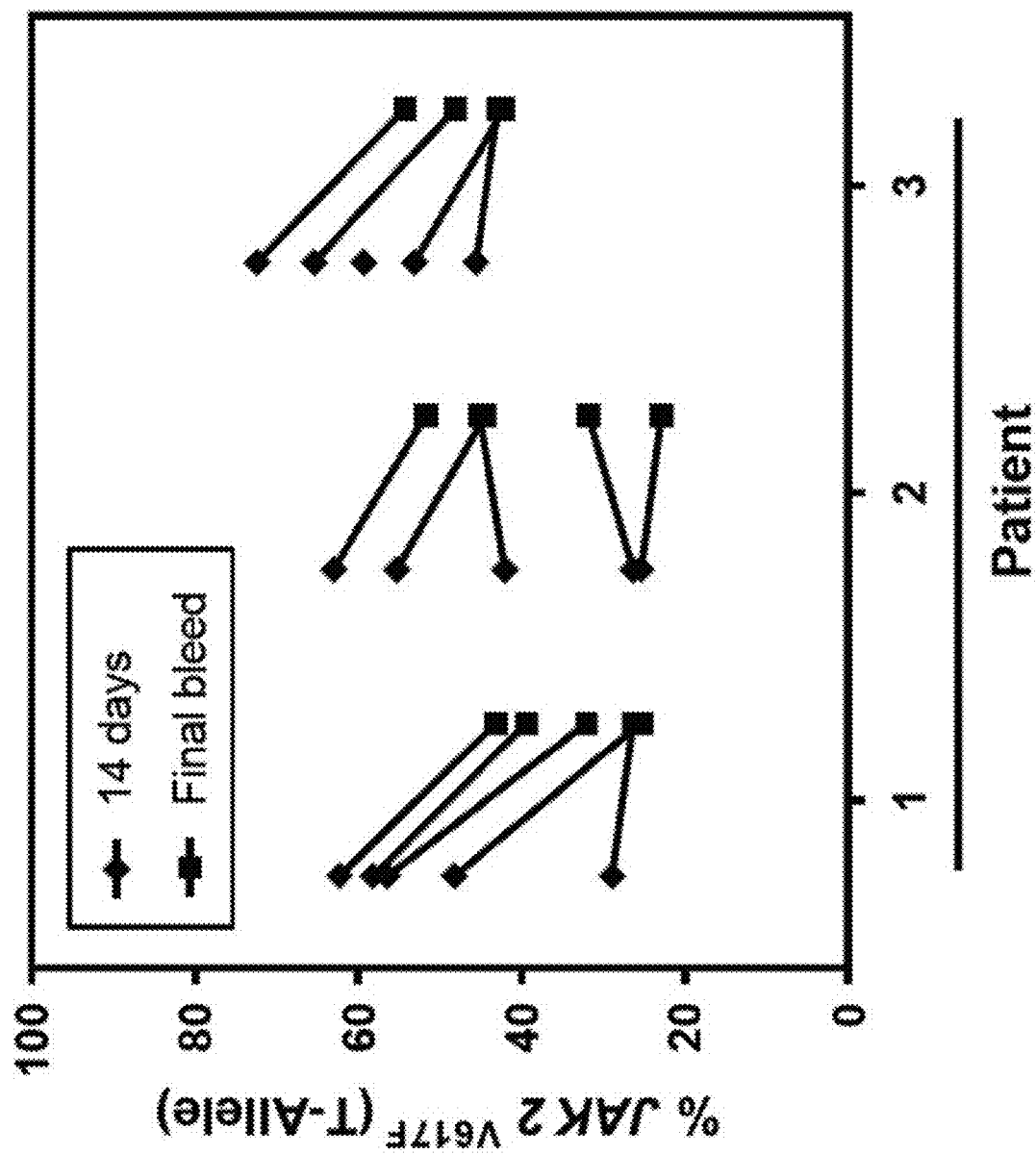
FIG. 5 indicates high mutant JAK2V617F allele burden is detected in NSG mice transplanted with PMF-derived CD14$^+$ cells, as discussed in Example 1. The levels of human JAK2V617F allele burden were measured in blood samples of NSG mice transplanted with CD14$^-$/CD34$^-$ BM cells obtained from PMF patient with a JAK2V617F mutation. Depicted are the JAK2V617F allele burdens of 15 mice transplanted with CD14$^+$/CD34$^-$ cells from 3 different PMF patients. The animals' blood was obtained 2 weeks after transplantation and before the animals were euthanized (final bleed). Although there is apparent decline in the JAK2V617F allele burden at the time of final bleed, the human mutant JAK2 variant was still detected at a significant measurable level several months after transplantation.

To confirm that engraftment of human neoplastic BM monocytes persisted, we systematically assessed the level of patient-derived JAK2V617F mutated neoplastic cells in the BM of mice transplanted with PMF monocytes. Using qASSPCR, we detected in BM cells of mice euthanized at 30, 60, 90, 120, and 150 days after transplantation a JAK2V617F allele burden of 22.1±19%, 37.5±8%, 26.3±18%, 42.2±10%, and 39.5±2%, respectively. To further determine that engraftment of the PMF $CD14^+$ cell-derived clone persists in the transplanted mice, we measured the levels of human JAK2V617F allele burden in the blood of NSG mice transplanted with JAK2-positive $CD14^+/CD34-$ cells 2 weeks after transplantation and before the animals were euthanized (final bleed). Although we observed a decline in the JAK2V617F allele burden at the time of final bleed, the human mutant JAK2 variant was still detectable at a significant level several months after transplantation (FIG. 5).

Figure 6:
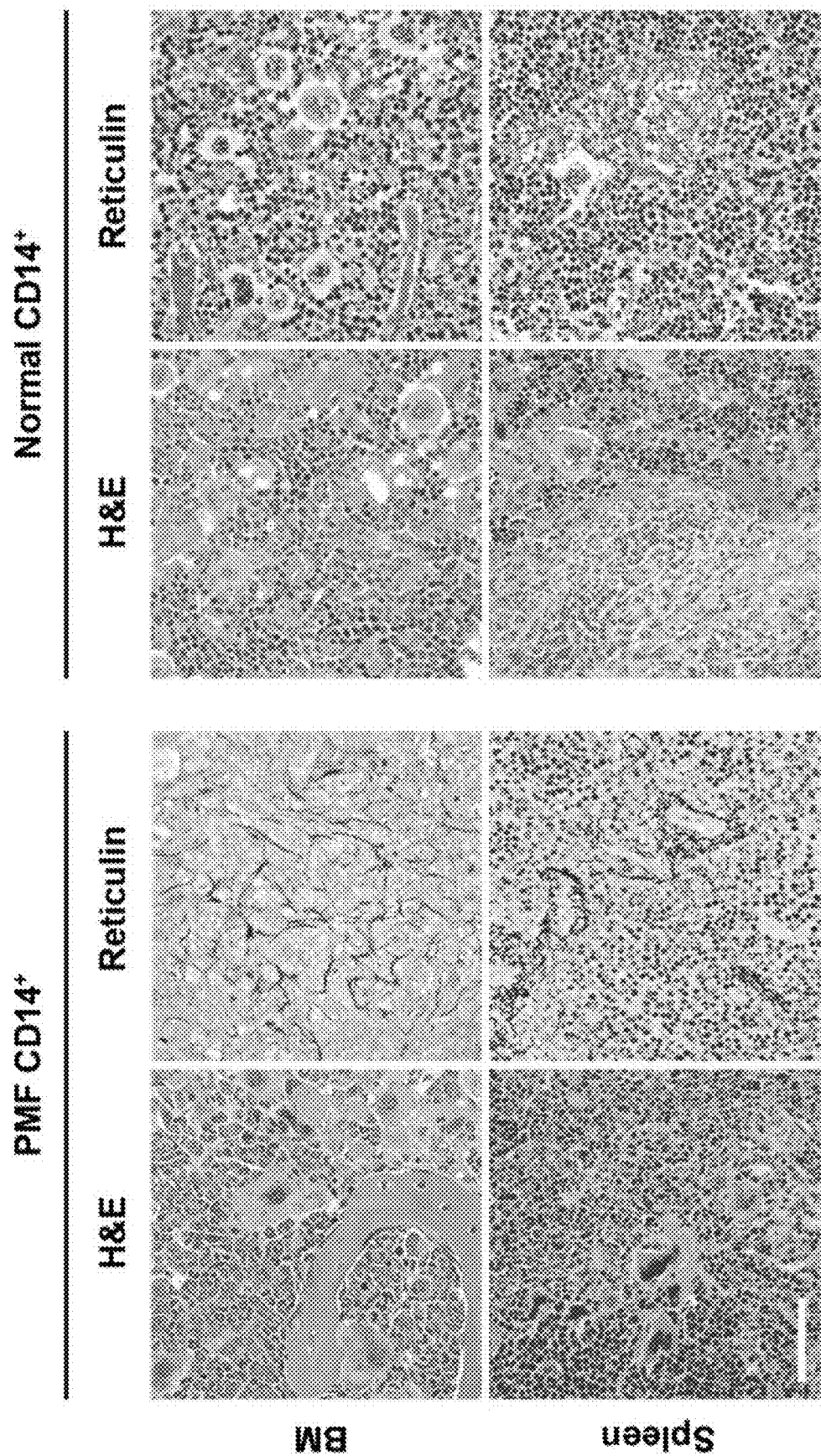
FIG. 6 shows BM and spleen fibrosis is readily detected in NSG mice transplanted with PMF, but not normal, CD14$^-$/CD34$^-$ BM cells, as discussed in Example 1. H&E and reticuline staining of BM (femur or sternum) and spleen sections of mice injected with PMF (left panel) or normal BM CD14$^+$/CD34$^-$ cells (right panel) are depicted. Notable features in PMF BM-transplanted mice include atypical megakaryopoiesis, anisocytosis, abnormal large nuclear/cytoplasmic ratio, hyperchromatic nuclei and plump lobulation of the nuclei. Reticuline-stained BM and spleen sections from mice injected with PMF BM-derived CD14$^+$/CD34$^-$ cells (left panel) show increased reticuline fibrosis. In contrast, in mice injected with normal BM-derived CD14$^+$/CD34$^-$ cells (right panel) hematopoiesis is unaltered, splenic architecture is preserved, and no significant reticuline fiber deposition is observed. Biopsies were taken after the animals were euthanized (median time following transplantation, 12 weeks). Bar, 50 µm.
Figure 7:
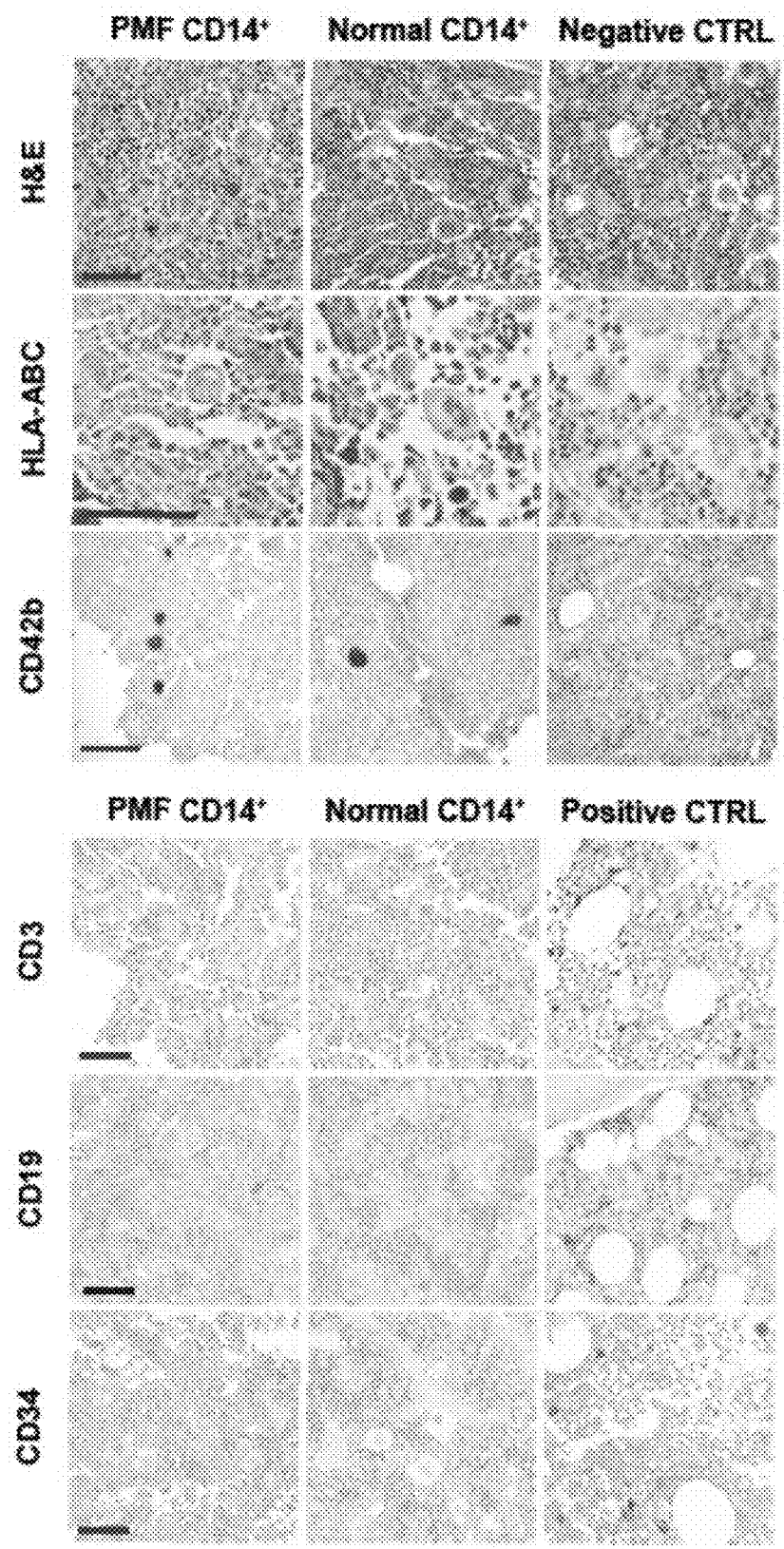
FIG. 7 demonstrates that megakaryocytes in the BM of mice transplanted with human BM CD14$^+$/CD34$^-$ cells in Example 1 are human-derived. Representative images of mouse femur or sternum BM sections are depicted. Human leukocyte antigen (HLA)-ABC− and human CD42b-positive megakaryocytes (upper panel), but no human CD3+, CD19+ or CD34+ cells (lower panel), were detected by immunohistochemistry in the BM of mice transplanted with either PMF BM-derived CD14$^+$/CD34$^-$ monocytes (left panel) or normal BM-derived CD14$^+$/CD34$^-$ monocytes (middle panel). HLA-ABC+ or human CD42b+ megakaryocytes were not detected in the BM of untransplanted mice (Negative CTRL; right upper panel), whereas CD3+, CD19+ and CD34+ cells were detected in the normal human BM (Positive CTRL; right lower panel). Bars, 50 µm.
Figure 8:
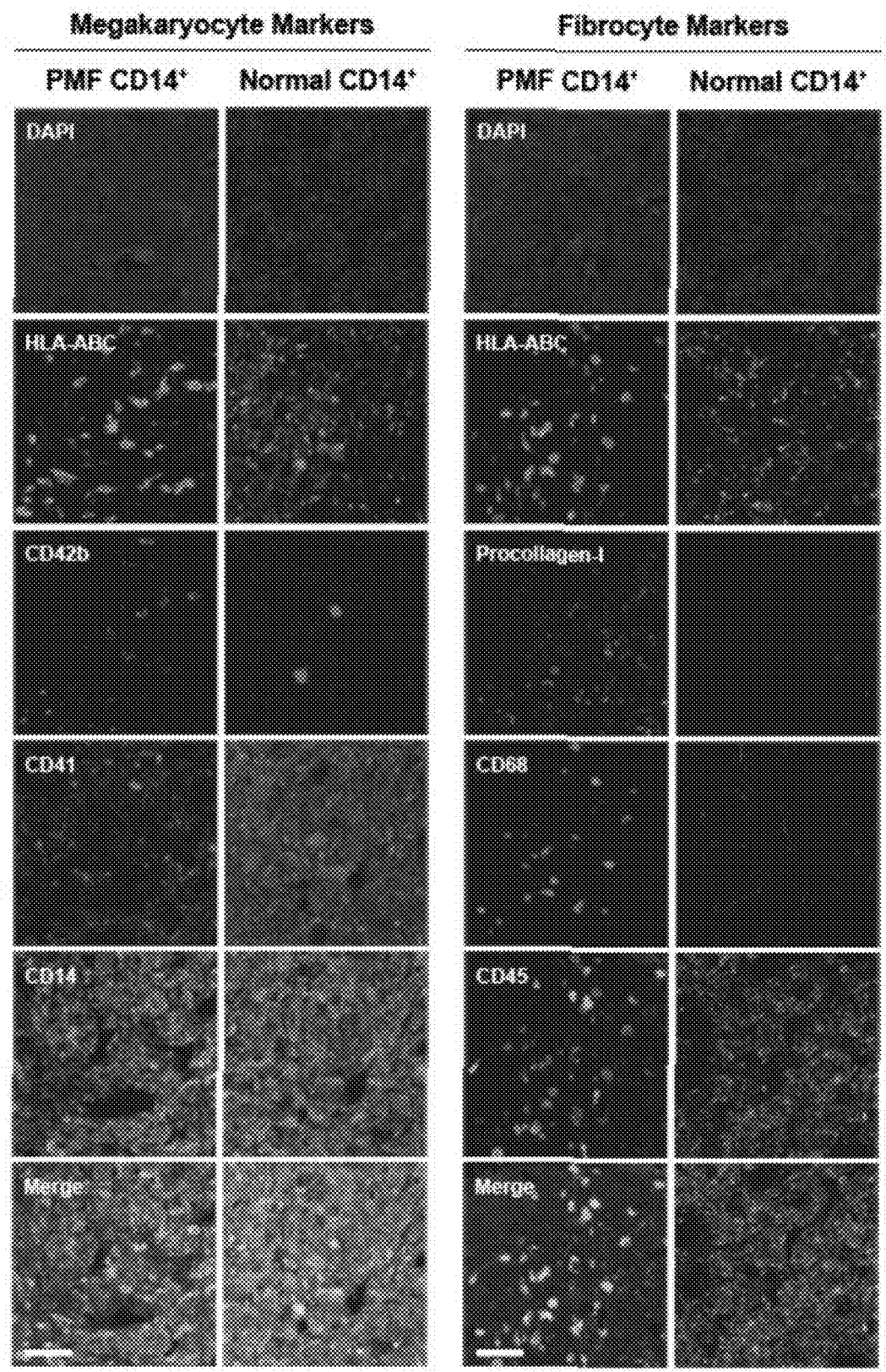
FIG. 8 shows that PMF and normal BM-derived CD14$^+$ cells transplanted into NSG mice give rise to human megakaryocytes, whereas PMF, but not normal BM CD14$^+$ cells give rise to human fibrocytes in the experiments of Example 1. Representative images of HLA-ABC+ cells in the BM of mice following injection of PMF (n=3) and normal human BM CD14$^+$ cells (n=2) are depicted. Expression of megakaryocyte (CD41, CD42b; left panel), and fibrocyte markers (CD45, CD68, procollagen-I; right panel) was assessed using multiplexed fluorescence IHC. Nuclei were counterstained using DAPI. Multiple large HLA-ABC+/CD41+/CD42b+ cells corresponding to human megakaryocytes, are observed in the BM of mice injected with PMF or normal CD14$^+$ cells (left lower panel; Merge). In contrast, spindle-shaped HLA-ABC+/CD45+/CD68+/procollagen-I+ cells, corresponding to human fibrocytes, are observed in the BM of mice injected with PMF patients' but not normal BM-derived CD14$^+$ cells (right lower panel; Merge). Due to cross-reactivity of the CD41 antibodies with mouse cells some HLA-ABC− cells appear to express CD41. No gamma correction was applied. Bars, 50 µm.

Like in patients with PMF and NSG mice transplanted with PMF BM low-density cells,[8] clusters of atypical megakaryocytes with abnormal large nuclear/cytoplasmic ratio, hyperchromatic nuclei with plump nuclear lobulation were identified in the BM and spleen of NSG mice that were transplanted with PMF BM-derived $CD14^+/CD34-$ monocytes (FIG. 6). To assess whether those atypical megakaryocytes were human- or mouse-derived, we used immunohistochemistry. Using this staining we detected megakaryocytes expressing HLA-ABC and human CD42b antigens in BM and spleen biopsy specimens of mice that were transplanted with PMF $CD14^+/CD34-$ monocytes. Similarly, we detected morphologically normal megakaryocytes expressing HLA-ABC and human CD42b antigens in the BM and spleen biopsies of mice that were transplanted with normal BM-derived CD14+/CD34− monocytes but not in BM or spleen biopsies of untransplanted mice (FIG. 7). Then, to determine whether BM-derived CD14+/CD34− cells gave rise to cells of other hematopoietic lineages we used immunohistochemistry. These stainings did not detect cells expressing human CD3, CD19 or CD34 antigens in all BM and spleen sections of mice transplanted with either PMF or normal monocytes (FIG. 7). Further analysis confirmed that PMF and normal BM CD14+/CD34− cells transplanted into NSG mice, gave rise to human megakaryocytes (FIG. 8; left panel) whereas PMF, but not normal BM CD14−/CD34− cells gave rise to human fibrocytes as assessed by fluorescent immunostaining of BM sections of mice injected with PMF (n=3) or normal BM CD14+ cells (n=2), using megakaryocyte (CD41, CD42b), and fibrocyte (CD45, CD68, procollagen-I) markers (FIG. 8; right panel). Taken together, these data suggested that human BM-derived CD14+/CD34− monocytes engrafted in NSG mice and gave rise to human megakaryocytes and fibrocytes.

Figure 9:
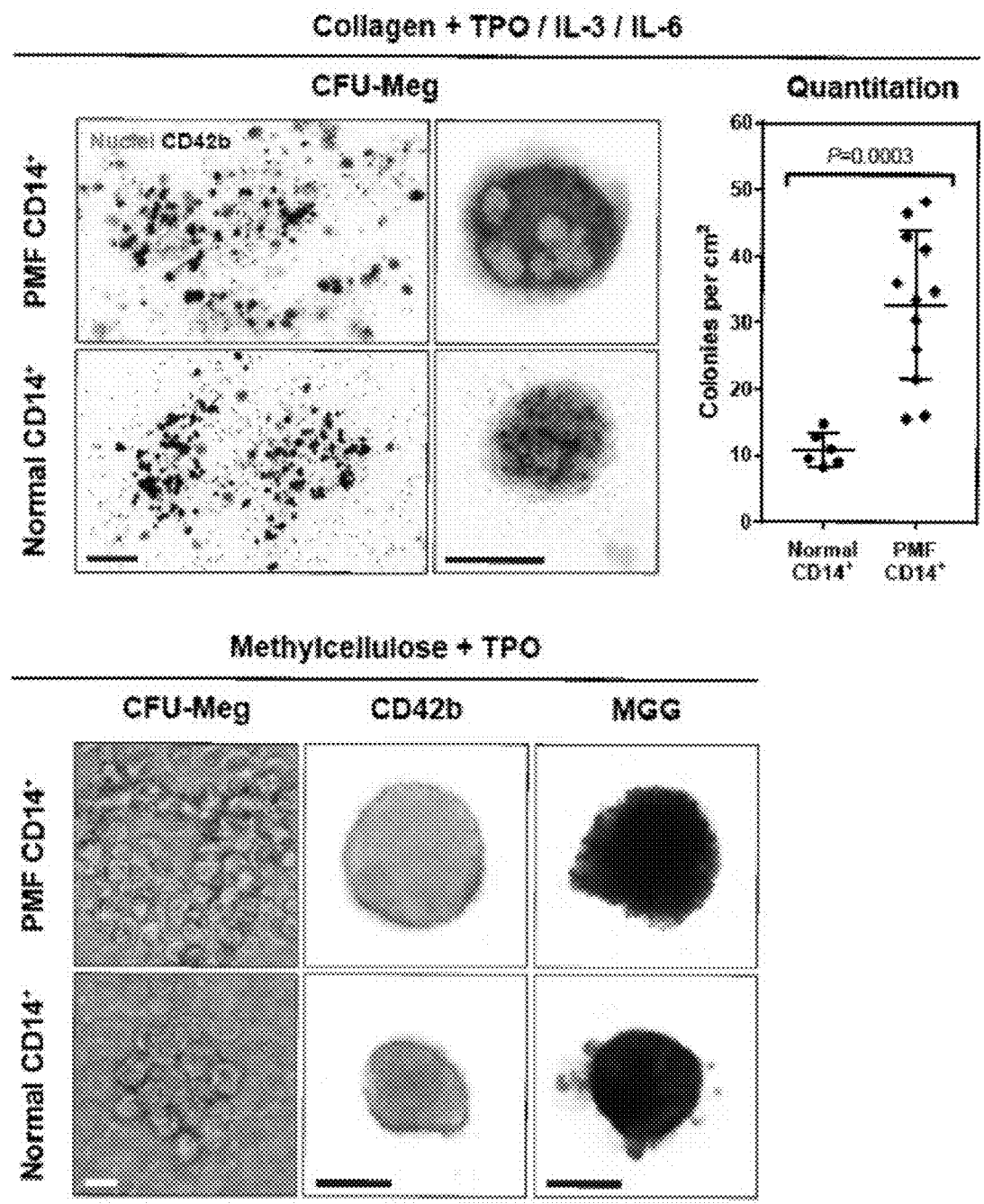
FIG. 9 shows that PMF and normal BM monocytes give rise to megakaryocyte colony-forming cells, as discussed in Example 1. Depicted are representative images of CFU-Meg colonies grown in collagen medium in the presence of thrombopoietin (TPO), interleukin-3 (IL-3) and IL-6 (upper panel) and CFU-Meg colonies grown in methylcellulose with addition of TPO alone (lower panel). Colonies in the collagen assay were fixed, stained with CD42b antibodies (Vector Blue) and counterstained with nuclear fast red. Megakaryocyte colonies were defined as clusters of 3 or more nucleated CD42b+ cells (left upper panel). Enlarged images of the CFU-Meg colonies identified mature megakaryocytes with multi-lobulated nuclei and high cytoplasm-to-nucleus ratio (middle upper panel). Cultures were scored based on total number of colonies counted inside the slide area. As shown (right upper panel), PMF $CD14^+$ cells gave rise to a higher number of CFU-Meg colonies than normal $CD14^+$ BM cells. Lines with error bars represent mean and standard deviation. Single colonies grown in the methylcellulose culture assay (left lower panel) were microaspirated, cytospun and stained with May-Grünwald-Giemsa (MGG) (right lower panel), and immunostained with anti-CD42b antibodies (middle lower panel), showing that the colonies consisted of micro-megakaryocytes that express CD42b cell surface antigen, typically detected in megakaryocytes. Bars, 100 µm (upper left panel), 20 µm (middle upper panel and lower panels).
Figure 10:
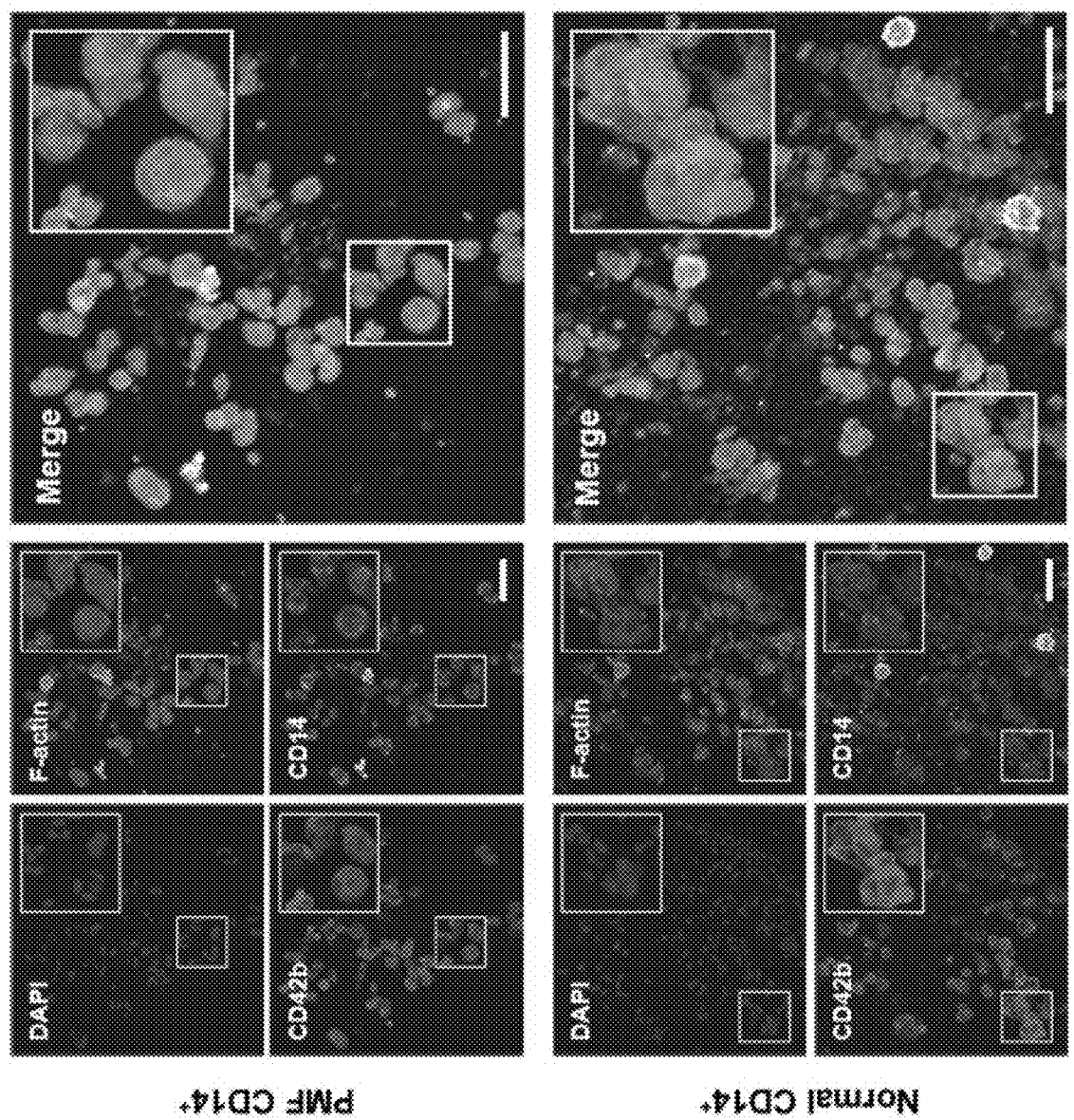
FIG. 10 shows immunofluorescence staining of the CFU-Meg colonies grown in collagen culture medium in Example 1. Representative confocal images of single CFU-Meg colonies fluorescently stained with F-actin (Alexa Fluor 488 phalloidin), CD42b (Alexa Fluor 594) and CD14 (Alexa Fluor 647) antibodies and nuclear DAPI stain. Depicted are CFU-Meg colony-derived multi-lobulated megakaryocytes from PMF and normal BM monocytes. Z-stacks were acquired at Nyquist sampling frequency with a 0.44-µm step size. No gamma adjustment was applied. Bars, 50 µm.
Figure 11:
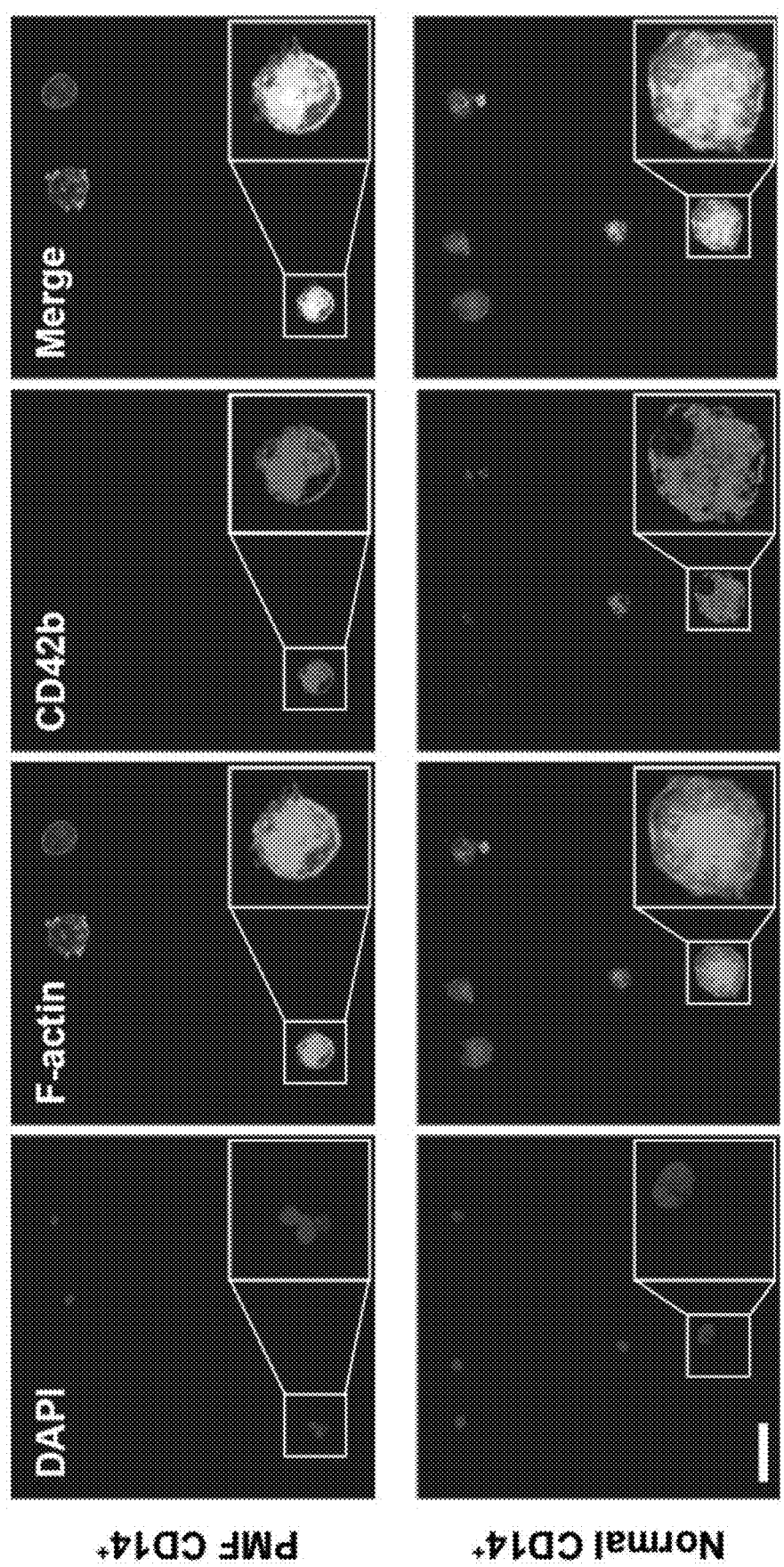
FIG. 11 shows immunofluorescent analysis of microaspirated PMF and normal BM $CD14^+/CD34^-$ cell-derived megakaryocyte colonies generated in Example 1. CFU-Meg colonies were cultured in methylcellulose culture medium supplemented with thrombopoietin (TPO). Cells from microaspirated cytospun colonies were fluorescently stained using F-actin (Alexa Fluor 488 phalloidin) and CD42b (Alexa Fluor 594) antibodies. Multiple CD42b+ cells with or without nuclear lobulation corresponding to promegakaryocytes and micro-megakaryocytes, respectively. DAPI was used as the nuclear counterstain. No gamma adjustment was applied. Bars, 50 µm.

To further confirm these findings, we cultured 12 PMF and 6 normal BM-derived CD14−/CD34− cells in 2 different megakaryocyte colony culture assays. After 3 weeks in culture, PMF BM CD14+/CD34− cells gave rise to 25-35 megakaryocyte colonies whereas normal BM CD14+/CD34− cells gave rise to 10-15 colonies. Similarly, in the collagen culture assay PMF BM CD14+/CD34− gave rise to a larger number of colonies than normal BM CD14+/CD34− cells (FIG. 9, right upper panel). Immunocytochemistry (FIG. 9) and fluorescent immunostaining of colonies grown in the CFU-Meg collagen colony culture assay (FIG. 10), as well as cytospun single microaspirated colonies grown in the methylcellulose culture assay (FIG. 11), confirmed that the colonies consisted of megakaryocytes with lobulated nuclei or micro-megakaryocytes expressing CD42b, suggesting that a fraction of CD14+ BM monocytes harbor megakaryocyte colony-forming cell capacity.

Figure 12:
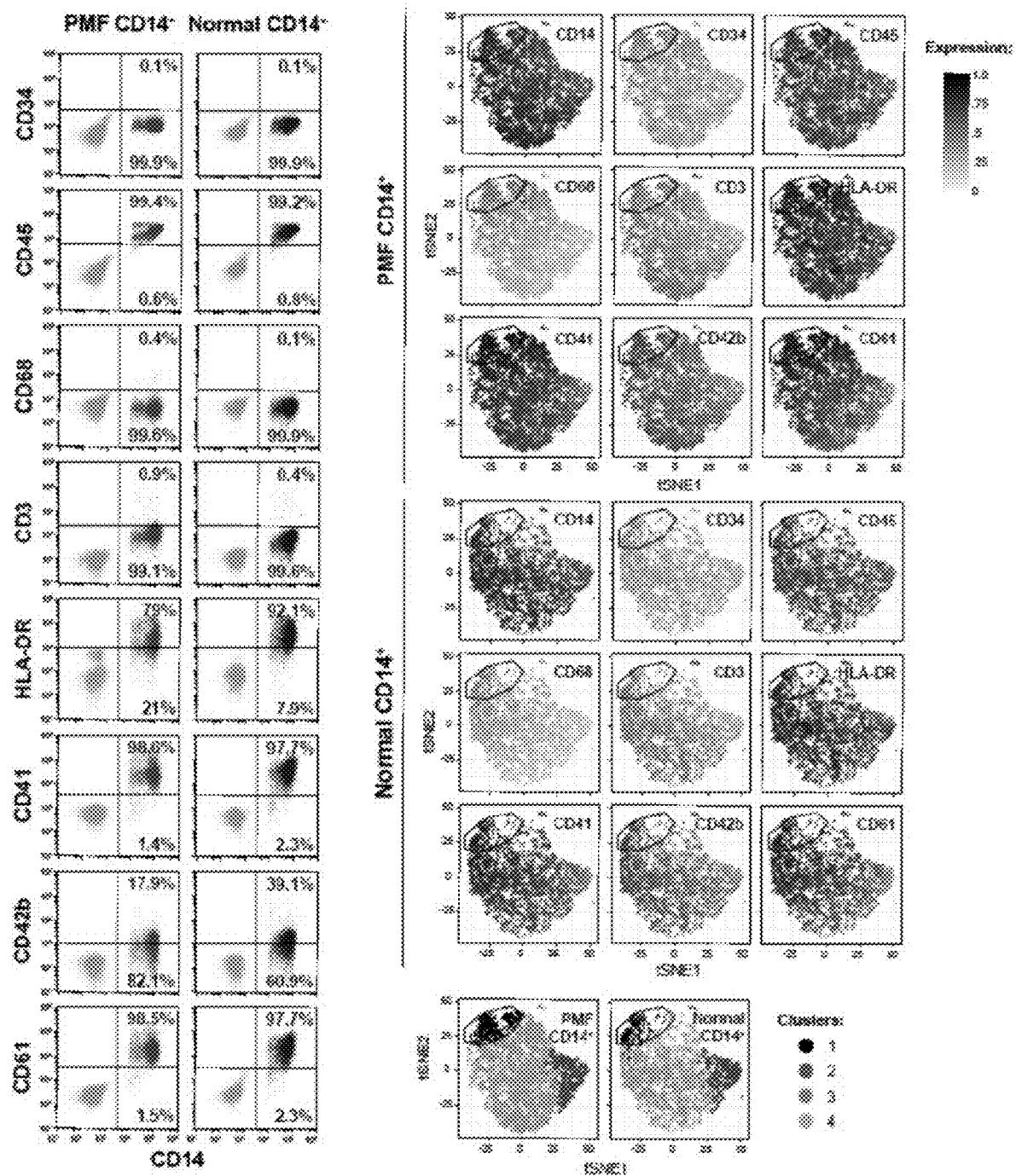
FIG. 12 presents immunophenotype data of PMF and normal BM-derived $CD14^+$ cells generated in Example 1. PMF (n=5) and normal BM-derived $CD14^+$ cells (n=3) were analyzed by flow cytometry using 9 lineage markers. The dot plots depict representative analyses of the 9 surface markers detected on $CD14^+$ cells (left panel), and the t-stochastic neighbor embedding (t-SNE) plots depict the cell-cell similarity based on the expression of all 9 markers (right upper panel) and corresponding cluster annotation (right lower panel). In addition to CD14 and CD34, expression profiles of CD45 (pan-leukocyte marker), CD68 (macrophage marker), CD3 (T-cell marker), HLA-DR (antigen-presenting cell marker) and CD41, CD42b and CD61 (megakaryocyte markers) are shown. In dot plots (left panel), red dots represent PMF cells, blue dots represent normal cells, and grey dots represent cells stained with the corresponding antibody's isotype control. Percentages of positive and negative populations of each marker were calculated using the depicted gates. In t-SNE plots (right panel), dots represent random 2,000 individual cells from each analyzed sample. For the purpose of clustering, all marker expressions were transformed using arcsin h (inverse hyperbolic sine) with a cofactor of 150. For visualization in t-SNE plots, expressions were further scaled to values between 0 and 1 using low (1%) and high (99%) percentiles as the boundary. The depicted gates represent computed boundaries of a cluster corresponding to megakaryocyte progenitors (cluster 1).

Because we found that a subpopulation of CD14+ monocytes harbors megakaryocyte progenitor capacity, we wondered whether a subset(s) of CD14+ monocytes expresses megakaryocyte lineage surface markers. To answer this question, we performed a high-parametric immunophenotype analysis of PMF and normal BM CD14+ cells. We found that the vast majority of CD14+ cells co-express CD45 and HLA-DR, but not CD34, CD68 or CD3 antigens (FIG. 12; left panel) and in agreement with previous reports, [12, 17-22] we found that subpopulations of PMF and normal CD14+ BM cells express the cell surface antigens CD41 and CD61, commonly detected on immature megakaryocytes, and CD42b, commonly detected on mature megakaryocytes. By performing unsupervised cluster analysis using all 9 markers, we identified a distinct subpopulation of CD14+ cells (cluster 1) that expresses all 3 megakaryocyte markers (FIG. 12; right panel). The CD14+ cells that expressed megakaryocyte antigens were small round monocytes as assessed by lateral and forward scatter analysis and by morphological criteria, indicating that subsets of CD14+ BM monocytes are primed to differentiate into cells of the megakaryocyte lineage.

Taken together, our data suggest that PMF and normal BM CD14+/CD34− monocytes engraft in NSG mice and that PMF BM fibrocyte precursor CD14+/CD34− monocytes induce a PMF-like phenotype with splenomegaly and BM fibrosis in NSG mice. In addition, our data suggest that a subpopulation of CD14+/CD34− monocytes give rise to CFU-Meg but not an upstream progenitor cell.[23] Whether monocyte-derived megakaryocytes play a role in the pathogenesis of PMF remains to be determined.

REFERENCES

1. Thiele J, Kvasnicka H M. Grade of bone marrow fibrosis is associated with relevant hematological findings—a clinicopathological study on 865 patients with chronic idiopathic myelofibrosis. Ann Hematol. 2006; 85(4):226-32. Epub 2006/01/20. https://doi.org/10.1007/s00277-005-0042-8 PMID: 16421727.
2. Vener C, Fracchiolla N S, Gianelli U, Calori R, Radaelli F, Iurlo A, et al. Prognostic implications of the European consensus for grading of bone marrow fibrosis in chronic idiopathic myelofibrosis2008 2008-02-15 00:00:00. 1862-5 p.
3. Rampal R, Al-Shahrour F, Abdel-Wahab O, Patel J P, Brunel J P, Mermel C H, et al. Integrated genomic analysis illustrates the central role of JAK-STAT pathway activation in myeloproliferative neoplasm pathogenesis. Blood. 2014; 123(22):e123-33. Epub 2014/04/18. https://doi.org/10.1182/blood-2014-02-554634 PMID: 24740812; PubMed Central PMCID: PMC4041169.
4. Verstovsek S, Mesa R A, Gotlib J, Levy R S, Gupta V, DiPersio J F, et al. A double-blind, placebo-controlled trial of ruxolitinib for myelofibrosis. N Engl J Med. 2012; 366(9):799-807. https://doi.org/10.1056/NEJMoa1110557 PMID: 22375971.
5. McLornan D P, Mead A J, Jackson G, Harrison C N. Allogeneic stem cell transplantation for myelofibrosis in 2012. Br J Haematol. 2012; 157(4):413-25. https://doi.org/10.1111/j.1365-2141.2012.09107.x PMID: 22463701.
6. Groopman J E. The pathogenesis of myelofibrosis in myeloproliferative disorders. Ann Intern Med. 1980; 92(6):857-8. https://doi.org/10.7326/0003-4819-92-6-857 PMID: 7387029.
7. Vannucchi A M, Bianchi L, Paoletti F, Pancrazzi A, Torre E, Nishikawa M, et al. A pathobiologic pathway linking thrombopoietin, GATA-1, and TGF-beta1 in the development of myelofibrosis. Blood. 2005; 105 (9):3493-501. https://doi.org/10.1182/blood-2004-04-1320 PMID: 15665119.
8. Verstovsek S, Manshouri T, Pilling D, Bueso-Ramos C E, Newberry K J, Prijic S, et al. Role of neoplastic monocyte-derived fibrocytes in primary myelofibrosis. J Exp Med. 2016; 213(9):1723-40. https://doi.org/10.1084/jem.20160283 PMID: 27481130; PubMed Central PMCID: PMC4995084.
9. Bucala R, Spiegel L A, Chesney J, Hogan M, Cerami A. Circulating fibrocytes define a new leukocyte subpopulation that mediates tissue repair. Mol Med. 1994; 1(1):71-81. PMC2229929. PMID: 8790603
10. Reilkoff R A, Bucala R, Herzog E L. Fibrocytes: emerging effector cells in chronic inflammation. Nat Rev Immunol. 2011; 11(6):427-35. Epub 2011/05/21. https://doi.org/10.1038/nri2990 PMID: 21597472; PubMed Central PMCID: PMC3599774.
11. Nowicka M, Krieg C, Weber L M, Hartmann F J, Guglietta S, Becher B, et al. CyTOF workflow: differential discovery in high-throughput high-dimensional cytometry datasets. F1000Research. 2017; 6:748-. https://doi.org/10.12688/f1000research.11622.3 MEDLINE: 28663787. PMID: 28663787
12. Hamers A A J, Dinh H Q, Thomas G D, Marcovecchio P, Blatchley A, Nakao C S, et al. Human Monocyte Heterogeneity as Revealed by High-Dimensional Mass 13. Quintas-Cardama A, Manshouri T, Estrov Z, Harris D, Zhang Y, Gaikwad A, et al. Preclinical characterization of atiprimod, a novel JAK2 and JAK3 inhibitor. Invest New Drugs. 2011; 29(5):818-26. Epub 2010/04/08. https://doi.org/10.1007/s10637-010-9429-z PMID: 20372971; PubMed Central PMCID: PMC4170651.
14. Thiele J, Kvasnicka H M, Facchetti F, Franco V, van der Walt J, Orazi A. European consensus on grading bone marrow fibrosis and assessment of cellularity. Haematologica. 2005; 90(8):1128-32. Epub 2005/08/05.16079113. PMID: 16079113
15. Stack E C, Wang C, Roman K A, Hoyt C C. Multiplexed immunohistochemistry, imaging, and quantitation: A review, with an assessment of Tyramide signal amplification, multispectral imaging and multiplex analysis. Methods. 2014; 70(1):46-58. https://doi.org/10.1016/j.ymeth.2014.08.016 WOS:000345199200008. PMID: 25242720
16. Hopman R K, DiPersio J F. Advances in stem cell mobilization. Blood Rev. 2014; 28(1):31-40. https://doi.org/10.1016/j.blre.2014.01.001. https://doi.org/10.1016/j.blre.2014.01.001 PMID: 24476957
17. Prieto J, Eklund A, Patarroyo M. Regulated expression of integrins and other adhesion molecules during differentiation of monocytes into macrophages. Cellular Immunology. 1994; 156(1):191-211. https://doi.org/10.1006/cimm.1994.1164 WOS:A1994NP11700017. PMID: 8200035
18. Lundahl J, Skold C M, Hallden G, Hallgren M, Eklund A. Monocyte and neutrophil adhesion to matrix proteins is selectively enhanced in the presence of inflammatory mediators. Scandinavian Journal of Immunology. 1996; 44(2):143-9. https://doi.org/10.1046/j.1365-3083.1996.d01-296.x WOS: A1996UZ88300008. PMID: 8711427
19. Law H K W, Bol S J L, Palatsides M, Williams N T. Analysis of human megakaryocytic cells using dualcolor immunofluorescence labeling. Cytometry. 2000; 41(4):308-15. https://doi.org/10.1002/1097-0320 (20001201) 41:4<308:aid-cyto9>3.0.co; 2-n WOS: 000165641900009. PMID: 11084616
20. Debili N, Robin C, Schiavon V, Letestu R, Pflumio F, Mitjavila-Garcia M T, et al. Different expression of CD41 on human lymphoid and myeloid progenitors from adults and neonates. Blood. 2001; 97 (7):2023-30. https://doi.org/10.1182/blood.v97.7.2023 WOS: 000168516000018. PMID: 11264167
21. Husheem M, Nyman J K E, Vaaraniemi J, Vaananen H K, Hentunen T A. Characterization of circulating human osteoclast progenitors: Development of in vitro resorption assay. Calcified Tissue International. 2005; 76(3):222-30. https://doi.org/10.1007/s00223-004-0123-z WOS: 000228213000007. PMID: 15692727
22. Passacquale G, Vamadevan P, Pereira L, Hamid C, Corrigall V, Ferro A. Monocyte-Platelet Interaction Induces a Pro-Inflammatory Phenotype in Circulating Monocytes. Plos One. 2011; 6(10). https://doi.org/10.1371/journal.pone.0025595 WOS:000295976000024. PMID: 22022418
23. Eaves C J. Hematopoietic stem cells: concepts, definitions, and the new reality. Blood. 2015; 125 (17):2605-13. Epub 2015/03/13. https://doi.org/10.1182/blood-2014-12-570200 PMID: 25762175; PubMed Central PMCID: PMC4440889.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of producing megakaryocytes, comprising:
    extracting cells from a tissue of a donor, wherein the tissue is selected from the group consisting of blood and bone marrow;
    isolating $CD14^+/CD34^-$ monocytes from the extracted cells; and
    culturing the isolated $CD14^{30}/CD34^-$ monocytes in vitro in the presence of thrombopoietin (TPO) for a sufficient time to permit differentiation of the $CD14^+/CD34^-$ monocytes into megakaryocytes.
2. The method of claim 1, wherein the sufficient time to permit differentiation is about 12 days or more.
3. The method of claim 1, wherein culturing the isolated $CD14^+/CD34^-$ monocytes in vitro is further in the presence of interleukin-3 (IL-3).
4. The method of claim 1, wherein the culturing the isolated $CD14^+/CD34^-$ monocytes in vitro is further in the presence of interleukin-6 (IL-6).
5. The method of claim 1, wherein culturing the isolated $CD14^+/CD34^-$ monocytes in vitro is further in the presence of a collagen.
6. The method of claim 1, wherein the megakaryocytes are CD42b positive.
7. The method of claim 1, wherein the megakaryocytes comprise multi-lobulated nuclei.
8. A method of producing platelets, the method comprising culturing the megakaryocytes produced by the method of claim 1 for a sufficient time to permit production of platelets.
9. The method of claim 8, further comprising combining the platelets with at least one of a buffer, preservative, adjuvant, surfactant, or diluent.
10. The method of claim 1, wherein the isolating is carried out using fluorescence-activated cell sorting (FACS) or a magnetic sorting column.
11. The method of claim 1, further comprising combining the megakaryocytes with at least one of a buffer, preservative, adjuvant, surfactant, or diluent.

* * * * *